United States Patent
Protzer et al.

(10) Patent No.: US 10,730,943 B2
(45) Date of Patent: Aug. 4, 2020

(54) MEANS AND METHODS FOR TREATING HBV INFECTION AND ASSOCIATED CONDITIONS

(71) Applicants: Helmholtz Zentrum München—Deutsches Forschungszentrum Für Gesundheit Und Umwelt (GMBH), Neuherberg (DE); Deutsches Krebsforschungszentrum, Heidelberg (DE)

(72) Inventors: Ulrike Protzer, München (DE); Felix Bohne, Münich (DE); Frank Momburg, Heidelberg (DE); Gerhard Moldenhauer, Bad Arolsen (DE)

(73) Assignees: Helmholtz Zentrum München-Deutsches Forschungszentrum Für Gesundheit Und Umwelt (GMBH), Neuherberg (DE); Deutsches Krebsforschungszentrum, Heidelberg (DE)

( * ) Notice: Subject to any disclaimer, the term of this patent is extended or adjusted under 35 U.S.C. 154(b) by 39 days.

(21) Appl. No.: 16/112,431

(22) Filed: Aug. 24, 2018

(65) Prior Publication Data
US 2018/0362649 A1 Dec. 20, 2018

Related U.S. Application Data

(62) Division of application No. 15/021,916, filed as application No. PCT/EP2014/069675 on Sep. 16, 2014, now Pat. No. 10,059,767.

(30) Foreign Application Priority Data

Sep. 16, 2013 (EP) .................................... 13184635

(51) Int. Cl.
| C07K 16/10 | (2006.01) |
| C07K 16/28 | (2006.01) |
| C12N 5/0783 | (2010.01) |
| C07K 16/08 | (2006.01) |
| A61K 39/00 | (2006.01) |

(52) U.S. Cl.
CPC ........ *C07K 16/2809* (2013.01); *C07K 16/082* (2013.01); *C07K 16/283* (2013.01); *C07K 16/2803* (2013.01); *C07K 16/2818* (2013.01); *C12N 5/0638* (2013.01); *C12N 5/0646* (2013.01); *A61K 2039/505* (2013.01); *A61K 2039/507* (2013.01); *C07K 2317/14* (2013.01); *C07K 2317/31* (2013.01); *C07K 2317/35* (2013.01); *C07K 2317/52* (2013.01); *C07K 2317/524* (2013.01); *C07K 2317/526* (2013.01); *C07K 2317/565* (2013.01); *C07K 2317/622* (2013.01); *C07K 2317/73* (2013.01); *C07K 2317/732* (2013.01); *C07K 2319/00* (2013.01)

(58) Field of Classification Search
None
See application file for complete search history.

(56) References Cited

U.S. PATENT DOCUMENTS

| 5,929,212 A | 7/1999 | Jolliffe et al. |
| 10,059,767 B2 | 8/2018 | Protzer et al. |
| 2005/0158829 A1 | 7/2005 | Fandl et al. |
| 2006/0127392 A1 | 6/2006 | de Romeuf et al. |
| 2010/0150918 A1 | 6/2010 | Kufer et al. |

FOREIGN PATENT DOCUMENTS

| EP | 2524699 A1 | 11/2012 |
| JP | 2005/501517 A | 1/2005 |
| JP | 2007-535915 A | 12/2007 |
| JP | 2016/530889 A | 10/2016 |
| WO | WO-0212437 A2 | 2/2002 |
| WO | WO-2008/119567 A2 | 10/2008 |
| WO | WO-2011/057124 A1 | 5/2011 |
| WO | WO-2012/156430 A1 | 11/2012 |
| WO | WO-2013/102123 A2 | 7/2013 |
| WO | WO-2015/036606 A1 | 3/2015 |

OTHER PUBLICATIONS

Bohne, F. et al., "T cells redirected against Hepatitis B virus surface proteins eliminate infected hepatocytes," Gastroenterology, 134:239-47 (2008).

(Continued)

*Primary Examiner* — Stacy B Chen
(74) *Attorney, Agent, or Firm* — Foley Hoag LLP

(57) ABSTRACT

The present invention relates to a polypeptide comprising (a) a first set of six complementarity determining regions (CDRs) configured to bind a first antigen; and (b) (ba) a second set of six CDRs configured to bind a second antigen; or (bb) a ligand capable of binding to a second antigen; wherein (i) said first antigen is selected from Hepatitis B virus (HBV) small surface antigen; HBV medium surface antigen; and HBV large surface antigen; and (ii) said second antigen is selected from surface antigens presented by immune effector cells such as natural killer (NK) cells and cytotoxic T lymphocytes (CTLs). Also provided are compositions for use in a method of treating or preventing HBV infection and/or a condition caused by said HBV infection, said condition caused by said HBV infection being selected from liver cirrhosis and hepatocellular carcinoma.

Figure 1:
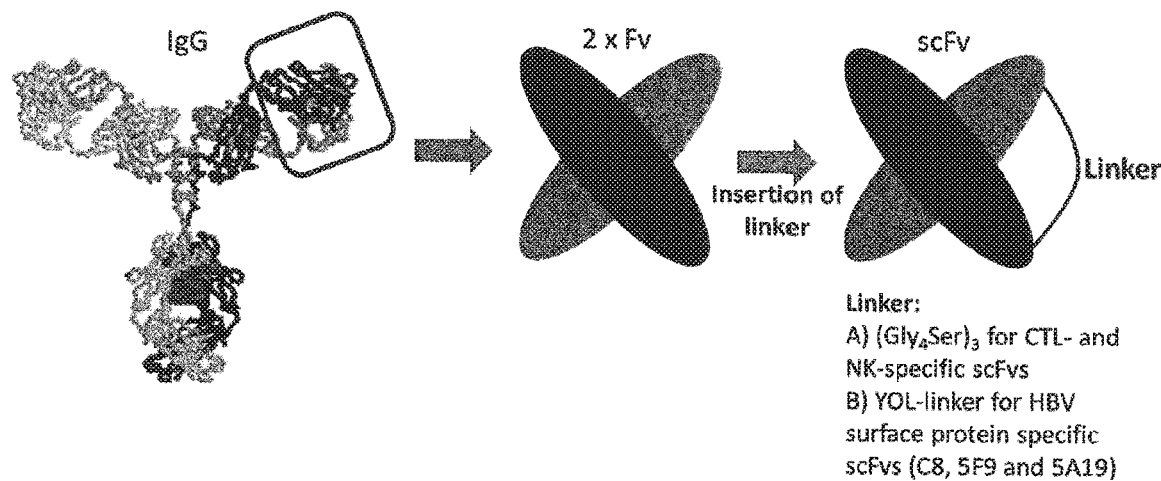

13 Claims, 14 Drawing Sheets
Specification includes a Sequence Listing.

(56) References Cited

OTHER PUBLICATIONS

Hornig, N. et al., "Production of bispecific antibodies: Diabodies and tandem scFv," Methods Mol Biol, 907:713-27 (2012).
International Search Report and Written Opinion, dated Jan. 5, 2015, from international application No. PCT/EP2014/069675.
Liao, Y. et al., "Preparation and application of anti-HBx/anti-CD3 bispecific monoclonal antibody (BsAb) retargeting effector cells for lysis of human hepatoma xenografts in nude mice," Oncol Rep, 3(4):637-44 (1996).
Pizarro et al., "Structural and Functional Characterization of a Monoclonal Antibody Specific for the preS1 Region of Hepatitis B Virus," FEBS Lett, 509(3): 463-468 (2001).
Pohl et al., "A Cassette Vector System for the Rapid Cloning and Production of Bispecific Tetravalent Antibodies," Antibodies, 1(1): 19-38 (2012).
Russian Search Report for International Application PCT/EP2014/069675, dated Sep. 14, 2014.
Yarilin, "Immunology Basics," M.: Medicine, pp. 172-174 (1999).
Kumagaya Izumi et al., Rinpakyu to Gan Saibo o Ninshikisuru Hitogata Nijyu-tokuiteki Kotai (Human type bispecefic antibody recognizing lymphocyte and cancer cell), Drug Delivery System, 23(5):518-525 (2008). (Abstract in English).
Cuesta et al., "Multivalent antibodies: when design surpasses evolution," Trends in biotechnology, 28(7):355-362 (2010).
Deyev et al., "Man-made antibodies and immunoconjugates with desired properties: function optimization using structural engineering," Russian Chemical Reviews, 84(1):1-26 (2015).
Deyev et al., "Multivalency: the hallmark of antibodies used for optimization of tumor targeting by design," Bioessays, 30(9):904-918 (2008).
Kipriyanov et al., "Generation and production of engineered antibodies," Molecular biotechnology, 26(1):39-60 (2004).
Souriau et al., "Recombinant antibodies for cancer diagnosis and therapy," Expert opinion on biological therapy, 3(2):305-318 (2003).
Li-Ping et al., "A New Model of Trispecific Antibody Resulting the Cytotoxicity Directed against Tumor Cells," Acta Biochimica et Biophysica Sinica, 35(6):503-510 (2003).
Liu et al., "A New Format of Single Chain Tri-specific Antibody with Diminished Molecular Size Efficiently Induces Ovarian Tumor Cell Killings," BioTech Letts 27(22):1821-1827 (2005).
Schoonjans et al., "Fab Chains as an Efficient Heterodimerization Scaffold for the Production of Recombinant Bispecific and Trispecific Antibody Derivatives," Journal of Immunology, 165:7050-7057 (2000).
Wang et al., "A New Recombinant Single Chain Trispecific Antibody Recruits T Lymphocytes to Kill CEA (Carcinoma Embryonic Antigen) Positive Tumor Cells In Vitro Efficiently," J. Biochem., 135(4):555-565 (2004).

MEANS AND METHODS FOR TREATING HBV INFECTION AND ASSOCIATED CONDITIONS

RELATED APPLICATIONS

This application is a divisional of U.S. patent application Ser. No. 15/021,916 filed Mar. 14, 2016 and issued as U.S. Pat. No. 10,059,767 on Aug. 28, 2018, which is a § 371 national-stage application based on PCT Application PCT/EP2014/069675, filed Sep. 16, 2014, the disclosures of which are hereby incorporated by reference in their entirety, and which claims priority to EP 13184635, filed Sep. 16, 2013.

The present invention relates to a polypeptide comprising (a) a first set of six complementarity determining regions (CDRs) configured to bind a first antigen; and (b) (ba) a second set of six CDRs configured to bind a second antigen; or (bb) a ligand capable of binding to a second antigen; wherein (i) said first antigen is selected from Hepatitis B virus (HBV) small surface antigen; HBV medium surface antigen; and HBV large surface antigen; and (ii) said second antigen is selected from surface antigens presented by immune effector cells such as natural killer (NK) cells and cytotoxic T lymphocytes (CTLs).

In this specification, a number of documents including patent applications and manufacturer's manuals is cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

About 350 million humans are chronically infected with hepatitis B virus (HBV). HBV infection may entail liver cirrhosis and hepatocellular carcinoma (HCC) which cause about one million casualties per year (Ganem et al., Hepatitis B virus infection—natural history and clinical consequences. N Engl J Med; 350:1118-29 (2004)). Infections with HBV presently cannot be controlled in about 5% of adult patients and about 90% of newborns. In such a case, the HBV infection becomes chronic. The likely cause is an insufficient cellular immune response. The presently available antiviral drugs, which are used for treatment of HBV infection, inhibit viral replication. However, the covalently closed circular DNA (cccDNA) remains in the nucleus of infected hepatocytes and may cause a reactivation of the HBV infection once the patient stops to take the medication. Therefore, it would be indispensable to eliminate HBV infected cells carrying said cccDNA if the infection were to be cured completely (Protzer et al., Nat Immunol Rev 12: 2013-213 (2012)).

However, such cytotoxic elimination of HBV infected cells (be it by cytotoxic T lymphocytes or natural killer (NK) cells) does not occur or not to a sufficient degree.

Infected cells carrying a HBV cccDNA display on their surface viral surface proteins. It is presumed that this occurs although the virus is released into intracellular vesicles because a number of HBV surface proteins remain integrated into the intracellular membrane of the endoplasmatic reticulum. In the course of vesicle transport processes said intracellular membrane may fuse with the cellular membrane, the consequence being that HBV surface proteins are displayed on the surface of the infected cell.

Bohne et al. (T cells redirected against hepatitis B virus surface proteins eliminate infected hepatocytes. Gastroenterology; 134:239-247 (2008)) and Krebs et al. (T Cells Expressing a Chimeric Antigen Receptor That Binds Hepatitis B Virus Envelope Proteins Control Virus Replication in Mice. Gastroenterology (2013)) describe chimeric antigen receptors which, when retrovirally delivered and expressed on the surface of a T cell, enable primary human and murine T cells to recognize hepatocytes displaying HBV small surface antigen and lyse HBV replicating cells.

Bispecific antibodies are typically employed in the field of oncology. As an example, we refer to Hartmann et al. (Treatment of refractory Hodgkin's disease with an anti-CD16/CD30 bispecific antibody. Blood; 89:2042-7 (1997)).

EP 2 524 699 A1 describes trifunctional antibodies. These antibodies "have a functional Fc portion" and "must consist of heavy immunoglobulin chains of different subclasses". Hornig und Färber-Schwarz on the other hand describe in Chapter 40 of "Antibody Engineering" (ed. Patrick Channes, Humane Press, 2012) an scFv construct which is devoid of the Fc portion.

Liao et al. (Oncology Reports 3, 637-644 (1996)) describe bispecific monochlonal antibodies retargeting effector cells for lysis of human hepatoma xenografts in nude mice. The bispecific antibodies described are generated by the fusion of two hybridomas, resulting in a hybridoma cell line expressing the heavy/light chain combinations of two distinct antibodies. This may result in pairing of the two different heavy chains, but also in the pairing of identical heavy chains, giving rise to a random mixture of monospecific parental and bi-specific antibodies. The bispecific antibodies contain heavy and light chain and dimerize to form an Ig molecule which is not a single polypeptide chain.

In view of the prior art, the technical problem could be seen in the provision of alternative or improved means and methods of treating HBV infection as well as conditions caused by HBV infection such as liver cirrhosis or hepatocellular carcinoma. Expressed in terms of cell biology, the technical problem can be seen in the provision of means and methods for the eradication of cells bearing HBV cccDNA. This technical problem is solved by the enclosed claims.

Accordingly, the present invention relates in a first aspect to a polypeptide comprising (a) a first set of six complementarity determining regions (CDRs) configured to bind a first antigen; and (b) (be) a second set of six CDRs configured to bind a second antigen; or (bb) a ligand capable of binding to a second antigen; wherein (i) said first antigen is selected from HBV small surface antigen; HBV medium surface antigen; and HBV large surface antigen; and (II) said second antigen is selected from surface antigens presented by immune effector cells such as natural killer (NK) cells and cytotoxic T lymphocytes (CTLs).

The term "polypeptide" defines a molecule which is a polycondensate of amino acids which form one single chain with one N-terminus and one C-terminus. The constituent amino acids include the 20 naturally occurring proteinogenic amino acids. Preferably, said polypeptide consists exclusively of said naturally occurring proteinogenic amino acids. Having said that, the term extends to molecules which, in addition to said naturally occurring proteinogenic amino acids, contain up to 20%, 10%, 5%, 2%, or 1% amino acids which are selected from non-naturally occurring α-amino acids, β-amino acids, D-amino acids, selenocysteine, selenomethionine, hydroxyproline, pyrrolysine and omithine. It is furthermore understood that one or more such as 2, 3, 4, 5, 6, 7, 8, 9 or 10 amino acids may be phosphorylated. The latter applies in particular to serine, threonine and tyrosine. Also other post-translational modifications as known in the art may be present including glycosylation. Glycosylations include N-linked glycosylations, typically at an asparagine and O-linked glycosylations, typically at serine or threonine residues. N- and/or C-terminus may be protected, protection groups including acetyl for the N-terminus and amine for the C-terminus. The type of linkage between the amino acids comprised in said polypeptide is confined to amide (CONH) bonds. The term "amide bond" includes peptide bonds which connect the α-carboxylate of a given amino acid to the α-amino group of the subsequent amino acid. The "amide bond" also extends to isopeptide bonds which is an amide bond that is not present on the main chain of the polypeptide. For example, instead of an α-amino group, the side chain amino group of lysine may be involved. Similarly, Instead of the α-carboxyl group, the side chain carboxylate of glutamate or aspartate may be involved. The occurrence of one or more such as 2, 3, 4, 5, 6, 7, 8, 9 or 10 isopeptide bonds is envisaged. Preference is given, though, to polypeptides wherein the constituent amino acids are linked to each other exclusively by peptide bonds.

In general, there is no upper limit on the number of amino acids in a polypeptide. As can be seen from the exemplary polypeptide sequences comprised in the sequence listing, the polypeptides of the present invention typically contain several hundred amino acids, preferably between 250 and 1000, 400 and 900, or between 700 and 800 amino acids. It is common to distinguish between peptides on the one hand and polypeptide on the other hand, wherein peptides have 30 or less amino acids and polypeptides have more than 30 amino acids.

The term "complementarity determining region", abbreviated as "CDR" has its meaning as established in the art. These are short subsequences, typically in the range from about 3 to about 25 amino acids, which confer to an antibody the capability to specifically recognize an epitope of an antigen. In general, the variable domain of the light chain of an antibody provides three CDRs and the variable domain of the heavy chain of an antibody provides three CDRs. While CDRs are typically part of immunoglobin domains, there is no requirement in that respect in accordance with the present invention. What is sufficient is an amino acid sequence, which comprises said CDRs provided that said amino acid sequence, when folded under physiological conditions, presents said CDRs in spatial proximity and maintains their capability to recognize the cognate antigen. The mentioned spatial proximity and capability of antigen binding is expressed by the term "configured to bind an antigen" as used in the above disclosed main embodiment. The term "immunoglobulin domain" is known in the art and refers to a sequence of typically 70 to 100 amino acids assuming a three-dimensional structure of a 2-layer sandwich of between 7 and 9 anti-parallel β-strands.

Said first set of six CDRs as well as said second set of six CDRs each define a binding site.

It is understood that beyond said first set and said second set no further CDRs are present in the polypeptide of the invention.

The term "antigen" has its art-established meaning. It refers to a molecule which is specifically recognized and bound by a set of six CDRs which typically are presented by immunoglobulin domains. The specific part of an antigen recognized and bound by said CDRs is also known as epitope.

The term "ligand" has its art-established meaning. A ligand is the counter-structure to a receptor. More specifically a ligand is capable of binding, preferably specifically binding to its cognate receptor. In accordance with the invention, said ligand is preferably an immunoligand. An immunoligand is a ligand which is capable of binding to a receptor present on the surface of an immune effector cell. Preferred immune effector cells are, as defined above, NK cells and CTLs. Preferred are those immunoligands which, when bound to their cognate receptor on the surface of an immune effector cell, exert a stimulating and/or co-stimulating effect. The terms "activate" and "stimulate" are used equivalently in this context. Receptors bound by preferred immunoligands are specified further below.

HBV S/M/L surface proteins are the small, medium and large surface proteins in the outer envelope of HBV (Stibbe, W., and W. H. Gerlich. Structural relationships between minor and major proteins of hepatitis B surface antigen. J. Virol. 1983 46:626-628).

The three HBV surface antigens are transcribed and translated from one reading frame and differ from each other by the length of the N-terminal part. Accordingly, the large surface antigen comprises a part which is neither present in the medium nor in the small surface antigen, and the medium surface antigen comprises a part which—while being comprised in the large antigen—is not comprised in the small antigen. The small antigen consists of a sequence, which is comprised in the C-terminal part of both the medium and the large antigen.

The large HBV surface antigen may be inserted in two manners in the cytoplasmic membrane. Either the N-terminus or the C-terminus may be located on the extracellular side. Both configurations are found in HBV infected cells.

The recited second antigen is a surface antigen presented by immune effector cells, preferably specifically presented by NK cells and/or CTLs. Immune effector cells are the cells to be redirected to HBV infected cells, said HBV infected cells presenting the mentioned HBV surface antigens on their surface.

It is particularly preferred that binding in accordance with the invention, in particular between CDRs and antigens as well as between ligands and antigens is specific. The terms "specifically binds" and "specifically binding" (having the same meaning as "specifically interacting") as used in accordance with the present invention mean that these binding portions do not or essentially do not cross-react with an epitope or a structure similar to that of the target antigen. Cross-reactivity of a panel of molecules under investigation may be tested, for example, by assessing binding of said panel of molecules under conventional conditions to the epitope of interest as well as to a number of more or less (structurally and/or functionally) closely related epitopes. Only those molecules that bind to the epitope of interest in its relevant context (e.g. a specific motif in the structure of a protein) but do not or do not essentially bind to any of the other epitopes are considered specific for the epitope of interest.

The first aspect comprises embodiments wherein items (a) and (ba) together are the only binding sites present on said polypeptide as well as embodiments wherein items (a) and (bb) together are only binding sites present on said polypeptide.

Chronic HBV infection is characterized by an immunotolerant status. More specifically, the patient's CTLs and NK cells perform such that a complete eradication of infected cells or a complete control of HBV replication or a complete elimination of HBV does not occur. The polypeptides according to the invention are bispecific molecules in the sense that they specifically recognize a HBV surface antigen on the one hand and an immune effector cell surface antigen on the other hand. Such bispecific molecules could be seen as conferring an artificial specificity to immune effector cells. In fact, CTLs and NK cells are retargeted by the polypeptides of the invention (also referred to as being "bispecific") such that they are recruited to HBV infected cells and kill them.

Binding of the polypeptides of the invention to HBV infected cells on the one hand and recruiting of immune effector cells on the other hand may occur in any order or also simultaneously.

In particular, it is intended to systemically apply polypeptides of the invention by either injection or as an oral application form and allow them to bind to HBV-infected or HBV antigen expressing target cells and recruit said immune effector cells to said target cells.

Having said that, it is also envisaged to bring polypeptides of the invention into contact with immune effector cells (or a population of peripheral blood mononuclear cells comprising said effector cells) such that said effector cells get loaded with said polypeptides. Such effector cells (or a population of PBMCs comprising such loaded effector cells) which have been loaded in vitro or ex vivo may then be administered to a patient suffering from HBV infection or a condition associated therewith and defined below. Such administering may be effected intravenously, e.g. to the *Arteria hepatica*. An immune effector cell with a polypeptide according to the present invention being bound to a surface antigen of said immune effector cell is also an aspect of the present invention. This aspect is disclosed further below.

This killing, in particular in conjunction with antiviral immune mediators (e.g. cytokines) as secreted by immune cells, provide for the eradication of HBV infection or for the sustained control of HBV infection or for the elimination of tumor cells expressing HBV surface antigens. Preferred or exemplary bispecific polypeptides in accordance with the present invention provide for astonishingly high killing rates of HBV-infected cells or liver tumor cells (also known as hepatoma cells) replicating HBV or expressing HBV surface antigens; see the examples enclosed herewith.

Given that bispecific polypeptides according to the present invention provide tailored specificities to immune effector cells, the naturally inherent specificity of the immune effector cells or the presentation of antigens to them becomes irrelevant. As such, a large pool of candidate effector cells is amenable to retargeting. Furthermore, the polypeptides of the invention have a bioavailability and half-life which is at least comparable to that of monoclonal antibodies.

In a preferred embodiment (a) said first set of six CDRs is comprised in a first scFv fragment; and/or (b) (ba) said second set of six CDRs is comprised in a second scFv fragment; or (bb) said ligand is an immunoligand, preferably capable of binding to NKG2D/CD314 (such as ligands MICA, MICB, ULBP1-6), NKp30/NCR3/CD337 (such as ligand B7-H6). 4-1BB/CD137 (such as ligand 4-1BB-L/CD137L) or OX40/CD134 (such as ligand OX40-L/CD252). A slash ("/") separates alternative art-established designations. In brackets preferred representatives of a given genus of antigens are provided.

The term "scFv" is well-established in the art. The abbreviation stands for "single chain variable fragment" of an antibody and defines a polypeptide capable of specifically recognizing and binding the epitope of an antigen. As noted above, three CDRs are presented by the variable domain of an antibody light chain ($V_L$) and three CDRs are presented by the variable domain of a heavy chain ($V_H$) of an antibody. In an scFv two variable domains are connected to each other by a peptide linker. The obtained fusion construct is a single polypeptide chain. This provides for easy expression of the scFv molecule. A schematic drawing can be found in FIG. 1.

The terms "$V_H$ domain" and "$V_L$ domain" are used according to the definitions provided in the art. Thus, they refer to the variable region of the heavy chain ($V_H$) and the variable region of the light chain ($V_L$) of immunoglobulins, respectively. Generally, $V_H$ and $V_L$ domains comprise three complementarity determining regions (CDRs) each, wherein CDRs are highly variable regions mainly responsible for the binding of the antigen.

A peptide linker is preferably used to link either variable regions of the scFv or to link the scFv to the dimerization and/or spacer region, preferably to the Fc. Typically the peptide linkers have a length between 3 and 30 amino acids, preferably between 5 and 25 or 10 and 20 amino acids. Preference is given to those linkers, which do not or not substantially interfere with structure and or function of the domains or polypeptides they connect (connecting yields a single continuous polypeptide chain). Linkers Include Gly-rich linkers such as the $(Gly_4Ser)_3$ (SEQ ID NO: 47) linker which is used in the preferred polypeptides of the Invention for connecting the $V_H/V_L$ domains of CTL or NK specific scFvs, and the Yol linker (SEQ ID NO: 48; AKTTP-KLEEGEFSEARV, as described in Sellrie et al., Journal of Biochemistry and Molecular Biology, Vol. 40, No. 6, November 2007, pp. 875-880) which is used in the preferred polypeptides of the invention for connecting the $V_H/V_L$ domains of the scFvs specific for HBV surface antigens. Also the $(Gly_4Ser)_4$ linker (SEQ ID NO: 49) may be used for connecting the $V_H/V_L$ domains of the scFvs specific for HBV surface antigens.

The term "antibody" as used herein has its art-established meaning. Preferably, it refers to the monoclonal antibody. Monoclonal antibodies can be prepared, for example, by the techniques as originally described in Köhler and Milstein, Nature 256 (1975), 495, and Galfré, Meth. Enzymol. 73 (1981), 3, which comprise the fusion of mouse myeloma cells to spleen cells derived from immunized mammals with modifications developed by the art. Furthermore, antibodies or fragments thereof directed to the aforementioned HBV surface proteins can be obtained by using methods which are described, e.g., in Harlow and Lane "Antibodies, A Laboratory Manual", CSH Press, Cold Spring Harbor, 1988. The production of chimeric antibodies is described, for example, in WO89/09622. A further source of antibodies to be utilized in accordance with the present invention are so-called xenogenic antibodies. The general principle for the production of xenogenic antibodies such as human antibodies in mice is described in, e.g., WO 91/10741, WO 94/02602, WO 96/34096 and WO 96/33735. Antibodies to be employed in accordance with the invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA or polypeptide sequence underlying the amino acid sequence of an immunoglobulin chain are well known to the person skilled in the art; see, e.g., Sambrook, Molecular Cloning: A Laboratory Manual, Cold Spring Harbor Laboratory, Cold Spring Harbor, N.Y., 1989. Modifications of the polypeptides include also post-translational modifications such as glycosylations.

In a further preferred embodiment, said first set of six CDRs binds an epitope of said first antigen which epitope is located (a) in said HBV small surface antigen; or (b) in the part of said HBV large surface antigen which is not comprised by said HBV small surface antigen; or (c) in a part of said HBV large surface antigen which part varies in structure from said HBV small surface antigen.

Item (a) refers to epitopes present in the HBV small surface antigen. Owing to the above described relation between small, medium and large HBV surface antigen, the entire sequence of the small antigen is comprised in the medium and the large antigen. In general, but not necessarily, a three-dimensional epitope presented by the small surface antigen will also be presented by the medium and/or the large surface antigen.

In accordance with item (b) it is preferred that said part of said HBV large surface antigen is also not comprised by said HBV medium surface antigen. As regards item (c), it is understood that "varying in structure" includes epitopes of said HBV large surface antigen which comprise or consist of sequences which are part of the sequence of said HBV small surface antigen, wherein said epitopes are not present on said HBV small surface antigen. In accordance with item (c) it is furthermore preferred that said epitope is in a part of said HBV large surface antigen which part varies in structure also from said HBV medium surface antigen.

Said item (a), i.e. said first antigen being said HBV small surface antigen is particularly preferred in conjunction with all aspects and embodiments of this invention.

In accordance with items (b) and (c), the polypeptide will specifically recognize the large surface antigen of HBV.

In a further preferred embodiment said surface antigen presented by immune effector cells is selected from CD3, CD28, 4-1BB, OX40, CD16, CD56, NKG2D, and NKp30/NCR3. Accordingly, the present invention provides a polypeptide comprising (a) a first set of six complementarity determining regions (CDRs) configured to bind a first antigen; and (b) (ba) a second set of six CDRs configured to bind a second antigen; or (bb) a ligand capable of binding to a second antigen; wherein (i) said first antigen is selected from hepatitis B virus (HBV) small surface antigen; HBV medium surface antigen; and HBV large surface antigen; and (ii) said second antigen is selected from surface antigens presented by immune effector cells such as natural killer (NK) cells and cytotoxic T lymphocytes (CTLs), wherein (c) said first set of six CDRs is comprised in a first scFv fragment; and (d) (da) said second set of six CDRs is comprised in a second scFv fragment; or (db) said ligand is an immunoligand capable of binding to NKG2D such as ligands MICA, MICB, ULBP1-6; NKp30 such as ligand B7-H6, 4-1BB such as ligand 4-1BB-L; or OX40 such as ligand OX40-L; and wherein said surface antigen presented by immune effector cells is selected from CD3, CD28, 4-1BB, OX40, CD16, CD56, NKG2D, and NKp30.

CD3 stands for the CD3 epsilon chain, which is part of the CD3-T-cell receptor complex. (Borst, J. et al., The delta- and epsilon-chains of the human T3/T-cell receptor complex are distinct polypeptides. Nature. 1984. 312: 455-458).

CD28 is a major T cell costimulatory receptor. (Lesslauer, W. et al., T90/44 (9.3 antigen). A cell surface molecule with a function in human T cell activation. Eur. J. Immunol. 1986. 16: 1289-1296).

4-1BB (CD137) is a costimulatory receptor of activated T cells and NK cells. (Kwon, B. S. et al., cDNA sequences of two inducible T-cell genes. Proc. Natl. Acad. Sci. U.S.A. 1989. 86:1963-1967).

OX40 (CD134) is a secondary costimulatory receptor. (Arch, R. H. at al., Mol. Cell. Biol. 1998. 18: 558-565). 4-1BB and OX40 are members of a tumor necrosis factor (TNF) receptor family that bind TNF receptor-associated ligands and activate nuclear factor kappaB.

CD16 (FcγRIIIa) is a low affinity Fc receptor expressed by NK cells, a subset of activated cytotoxic T cells as well by cell types from the myelomonocytic lineage, binding to the Fc domain of IgG molecules. (Lanier, L. L. et al., Functional properties of a unique subset of cytotoxic CD3+T lymphocytes that express Fc receptors for IgG (CD16/Leu-11 antigen). J. Exp. Med. 1985. 162: 2089-2106).

CD56 (NCAM) is a cell adhesion molecule expressed by NK cells. (Lanier, L. L. et al., Identity of Leu-19 (CD56) leukocyte differentiation antigen and neural cell adhesion molecule. J. Exp. Med. 1989. 169: 2233-2238).

NKG2D is an activating receptor expressed by NK cells (Houchins, J. et al., DNA sequence analysis of NKG2, a family of related cDNA clones encoding type II integral membrane proteins on human natural killer cells. 1991. J. Exp. Med. 173: 1017-1020).

NKp30 (NCR3) is a receptor expressed by NK cells (Pende, D. et al., Identification and molecular characterization of NKp30, a novel triggering receptor involved in natural cytotoxicity mediated by human natural killer cells. 2000. J. Exp. Med. 192: 337-346).

CD3, CD28, 4-1BB and OX40 are present on the surface of CTLs. Binding of a polypeptide of the invention to any of these surface antigen entails stimulation or co-stimulation of CTLs.

CD16, CD56, NKG2D, NKp30/NCR3 and 4-1BB are present on the surface of NK cells. Binding of a polypeptide of the invention to any of these surface antigens entails stimulation or co-stimulation of NK cells.

With regard to human CTLs, preference is given to CD3 and CD28. With regard to human NK cells, preference is given to CD16 and CD56.

The mentioned surface antigens are designated by art-established names, (see also Kenneth Murphy, Janeway's Immunobiology, $7^{th}$ edition, Garland Science; William E. Paul, Fundamental Immunology, $7^{th}$ edition, Lippincott Williams & Wilkins).

In a further preferred embodiment, said polypeptide further comprises a dimerization region. Said dimerization region may provide for covalent and/or non-covalent dimerization.

Through dimerization the bispecific bivalent antibodies are rendered bispecific tetravalent (or even tetraspecific tetravalent if different bispecific antibodies are co-expressed in the producing cell). Bispecific tetravalent reagents as described here are expected to possess an augmented avidity that is similar to conventional monospecific antibodies since they are able to engage two antigen molecules of the same type with their N-terminal side and their C-terminal side, respectively.

In a particularly preferred embodiment, said dimerization region that connects two polypeptides of the invention consists of the hinge region of the IgG heavy chain or comprises the cysteine residues responsible for the dimerization of the heavy chains of an antibody. Preferably, said dimerization region consists of a subsequence of 32 amino acids in length, the so called hinge region of the heavy chain (EPKSSDKTHTCPPCPAPEFEGAPSVFLFPPKP, see SEQ ID NOs: 43 to 46) and comprises the two cysteine residues (underlined in above sequence) responsible for the dimerization of the heavy chains. Preferably the single cysteine residue within the hinge region of the IgG heavy chain that mediates the intermolecular disulfide bond between the IgG heavy and light chain constant domains in a natural antibody is mutated into a serine in order to prevent aberrant disulfide bridges.

Dimerization domains suitable for non-covalent dimerization are known in the art and include leucine zippers.

In a further preferred embodiment, said polypeptide further comprises a spacer region, said spacer region preferably comprising a CH2 domain and a CH3 domain, said spacer region being located between (i) said first scFv fragment and (ii) said second scFv fragment or said recombinant ligand in the amino acid sequence of said polypeptide.

A spacer region comprising or consisting of a CH2 domain and a CH3 domain, in particular from IgG, is advantageous. Their capability to bind protein A provides for an efficient secretion from producer cells and/or the subsequent purification from the reagents.

Both said CH2 and CH3 domain on the one hand and said dimerization region on the other hand may be provided by the corresponding region of an IgG, preferably IgG1 or IgG2 molecule, even more preferred a human IgG1 or IgG2 (hIgG1, hIgG2) molecule. A preferred subsequence of a hIgG1 molecule providing CH2 domain, CH3 domain and dimerization domain can be seen in sequences 43 to 46. Preferably—and this applies to the mentioned sequences—the portion of hIgG1, in particular said CH2 domain, was mutagenized in multiple positions to diminish or abolish the binding to Fc receptors (indicated in bold-face italics in the sequences given further below). More generally, the Fc region, in particular the $CH_2$ domain and/or the $CH_3$ domain may be mutated in one or more positions to diminish or abolish the binding to Fc receptors. Such procedure is known in the art and described, for example, in Armour et al., Recombinant human IgG molecules lacking Fcgamma receptor I binding and monocyte triggering activities. Eur. J. Immunol. 1999. 29: 2613-2624 and Lazar et al., Engineered antibody Fc variants with enhanced effector function. Proc. Natl. Acad. Sci. U.S.A. 2006. 103: 4005-4010. This is advantageous because triggering of antibody dependent cell-mediated cytotoxicity (ADCC) is not preferred in accordance with the invention.

In other words, an antibody Fc fragment may be used to implement spacer region and dimerization region. The term "Fc fragment" is known to the skilled person and defines a fragment of IgG which is obtained by cleavage with papain and comprises CH2 and CH3 domains.

Between said first scFv fragment and said spacer region and/or between said spacer region and said second scFv fragment (a) linker sequence(s) is/are present. Preferred linker sequences are disclosed herein above. As can be seen from the preferred sequences comprised in the sequence listing, in particular sequences of SEQ ID NOs: 43 to 46, such linker sequences may consist of glycines or glycines and serines.

Figure 2:
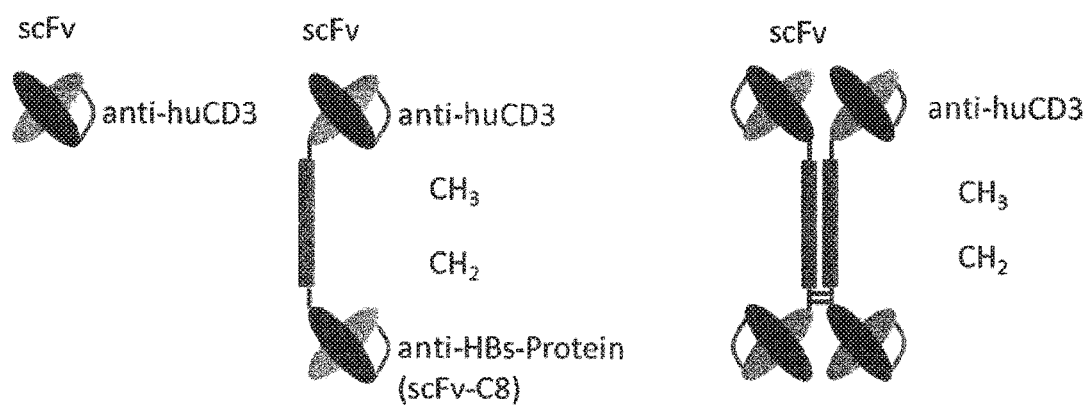

FIG. 2 illustrates the molecular architecture of those preferred polypeptides of the invention which comprise a dimerization region (hIgG hinge region) as well as a CH2 and a CH3 region separating the two scFv fragments from each other.

The terms "CH2 domain" and "CH3 domain" have its art-established meaning. They refer to the second and third constant domain of antibody heavy chains.

It is understood that a particularly preferred embodiment relates to a polypeptide comprising (a) a first set of six complementarity determining regions (CDRs) configured to bind a first antigen; and (b) (ba) a second set of six CDRs configured to bind a second antigen; or (bb) a ligand capable of binding to a second antigen; wherein (i) said first antigen is selected from hepatitis B virus (HBV) small surface antigen; HBV medium surface antigen; and HBV large surface antigen; and (ii) said second antigen is selected from surface antigens presented by immune effector cells such as natural killer (NK) cells and cytotoxic T lymphocytes (CTLs), wherein (c) said first set of six CDRs is comprised in a first scFv fragment; and (d) (da) said second set of six CDRs is comprised in a second scFv fragment; or (db) said ligand is an immunoligand, preferably capable of binding to NKG2D such as ligands MICA, MICB, ULBP1-6; NKp30 such as ligand B7-H6; 4-1BB such as ligand 4-1BB-L; or OX40 such as ligand OX40-L, wherein said surface antigen presented by immune effector cells is selected from CD3, CD28, 4-1BB, OX40, CD16, CD56, NKG2D, NKp30 and 4-1BB, and wherein said polypeptide further comprises a dimerization region and a spacer region, said dimerization region and said spacer region preferably being as further defined above.

In a further preferred embodiment, (a) said first set of six CDRs has the sequences of SEQ ID NOs: 1 to 6, 7 to 12 or 13 to 18; and/or (b) said second set of six CDRs has the sequences of SEQ ID NOs: 19 to 24, 25 to 30, 31 to 36 or 37 to 42.

As common in the art, and furthermore as evident from the enclosed sequence listing, the ordering of the CDRs in each set of six CDRs as specified above is as follows: CDR1 of heavy chain, CDR2 of heavy chain, CDR3 of heavy chain, CDR1 of light chain, CDR2 of light chain, and CDR3 of light chain.

C8, 5F9, 5A19, OKT3, 9.3, A9 and NCAM29.2 as used in the sequence listing designate the antibody from which the respective CDRs originate from and refer to a preferred anti-HBs antibody, to a second different anti-HBs antibody, an antibody against HBV large surface antigen, an antibody against human CD3, an antibody against human CD28, an antibody against human CD16, and an antibody against human CD56, respectively. "HBs" designates the HBV small surface antigen.

Particularly preferred is that said polypeptide comprises or consists of the amino acid sequence of any one of SEQ ID NOs: 43 to 46 or an amino acid sequence which exhibits at least 80% identity to any one of SEQ ID NOs: 43 to 46, provided that the CDRs of said amino acid sequence exhibiting at least 80% identity are identical to those comprised in any one of SEQ ID NOs: 43 to 46, respectively. In SEQ ID NO: 43, the last three residues "GNS" are dispensable.

Preferred levels of sequence identity include at least 85%, at least 90%, at least 91%, at least 92%, at least 93%, at least 94%, at least 95%, at least 96%, at least 97%, at least 98%, and at least 99%. Means and methods for determining sequence identity are well-known in the art. A preferred algorithm for determining pairwise sequence identity is the basic local alignment search tool (BLAST) as described, for example, in McGinnis and Madden (Nucleic Acid Research 32, W20-W25 (2004)).

The location of said CDRs in a given sequence, in the present case in the sequences of SEQ ID NOs: 43 to 46 can be determined with art-established methods, known art-established methods including the systems of Chothia, Kabat and LeFranc/IMGT, respectively. In the absence of any indication to the contrary, it is understood that the CDRs according to the above defined particularly preferred embodiment are those defined above, namely a first set having the sequences of SEQ ID NOs: 1 to 6, 7 to 12 or 13 to 18, and a second set having the sequences of SEQ ID NOs: 19 to 24, 25 to 30, 31 to 36 or 37 to 42. As can be seen from the sequences as comprised in the enclosed sequence listing, these specific CDR sequences (underlined in the sequences reproduced further below) are indeed comprised in the sequences of SEQ ID NOs: 43 to 46.

The sequences of SEQ ID NOs: 1 to 6 define the CDRs and SEQ ID NOs: 37 to 40 define bispecific polypeptides capable of binding a specific epitope within the small surface antigen of HBV. This epitope is located in the a-determinant, which is exposed to the surface of infected cells and virions, respectively. The term "a-determinant" Is used to designate a region within the small surface antigen of HBV where the main epitopes for induction of a protective humoral Immune response are located. These CDRs as well as the polypeptides of SEQ ID NOs: 43 to 46 have the advantage they can be used for all HBV serotypes.

In a second aspect, the present invention provides a nucleic acid encoding the polypeptides defined above. Preferred embodiments of the polypeptides give rise to corresponding preferred embodiments of said nucleic acid.

The term "nucleic acid" has its art-established meaning and is not particularly limited. Preferred are DNA such as genomic DNA or cDNA as well as RNA such as mRNA. While not being preferred, the use of nucleotide derivatives is envisaged which nucleotide derivatives include 2' derivatized nucleotides such as 2' methyl nucleotides; peptide nucleotides as the occur in peptide nucleic acids and the like.

In a third aspect, the present invention provides a covalently linked complex comprising or consisting of a first and a second polypeptide, wherein there is at least one covalent linkage between said first and said second polypeptide, preferably at least one disulfide bridge between a Cys residue of said first polypeptide and a Cys residue of said second polypeptide, said first and second polypeptides being as defined in accordance with the invention.

Preferred are two covalent linkages between said first and said second polypeptide, preferably two disulfide linkages as depicted in FIG. 2.

Also provided is a complex comprising or consisting of a first and a second polypeptide, wherein said first and said second polypeptide are bound to each other non-covalently.

An exemplary drawing of such covalently linked complex is shown in FIG. 2. Preference is given to said complex being a dimer.

In a fourth aspect, the present invention provides a composition comprising or consisting of one or more polypeptides according to the invention and/or one or more complexes according to the invention, provided that at least two polypeptides are comprised in said composition which two polypeptides are distinct from each other with regard to the first antigen and/or the second antigen to which they bind.

In a preferred embodiment of said fourth aspect, said two polypeptides are (a) (i) a polypeptide binding to HBV small or large surface antigen and CD3; and (ii) a polypeptide binding to HBV small or large surface antigen and CD28; or (b) (i) a polypeptide binding to HBV small or large surface antigen and CD16; and (ii) a polypeptide binding to HBV small or large surface antigen and CD56.

Both alternative (a) as well as alternative (b), in particular to the extent they relate to polypeptides binding to HBV small surface antigen, of this preferred embodiment provide for outstandingly high elimination rates of up to 95% as compared to the negative control. This is expected to provide for a complete eradication of HBV infected cells or HBV-antigen positive tumor cells, especially after repeated application in an in vivo situation.

Figure 3:
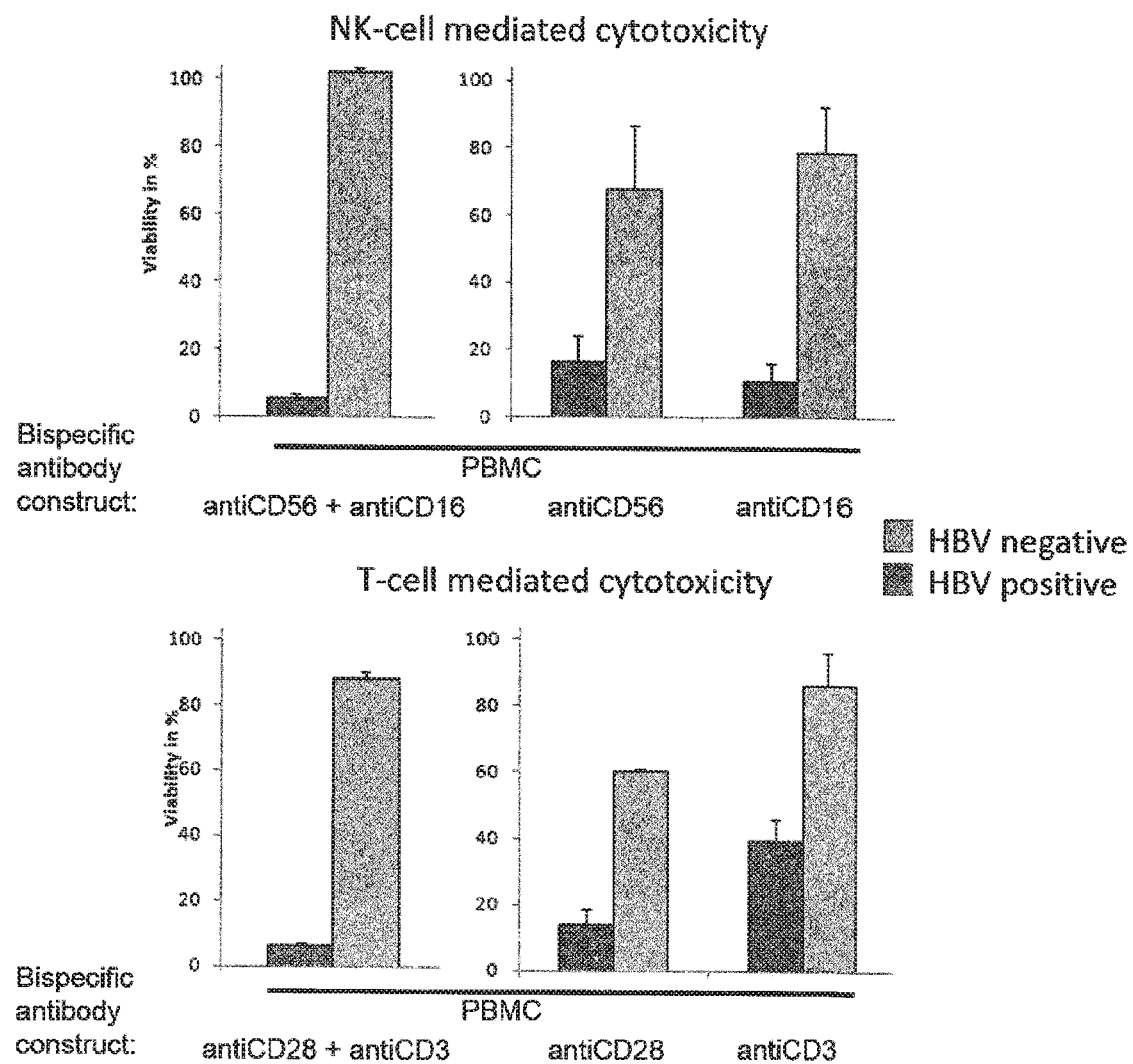
Figure 4:
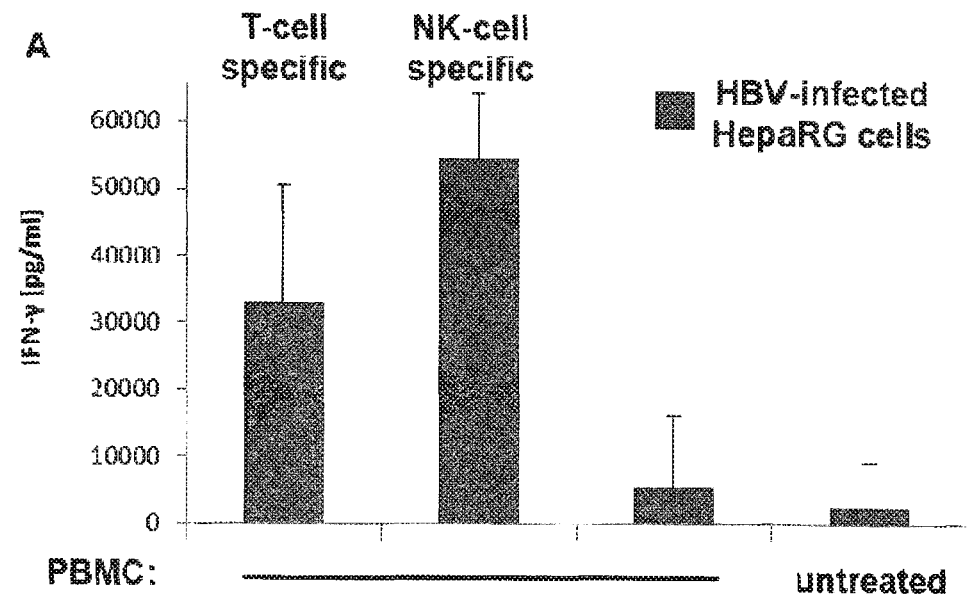
Figure 4:
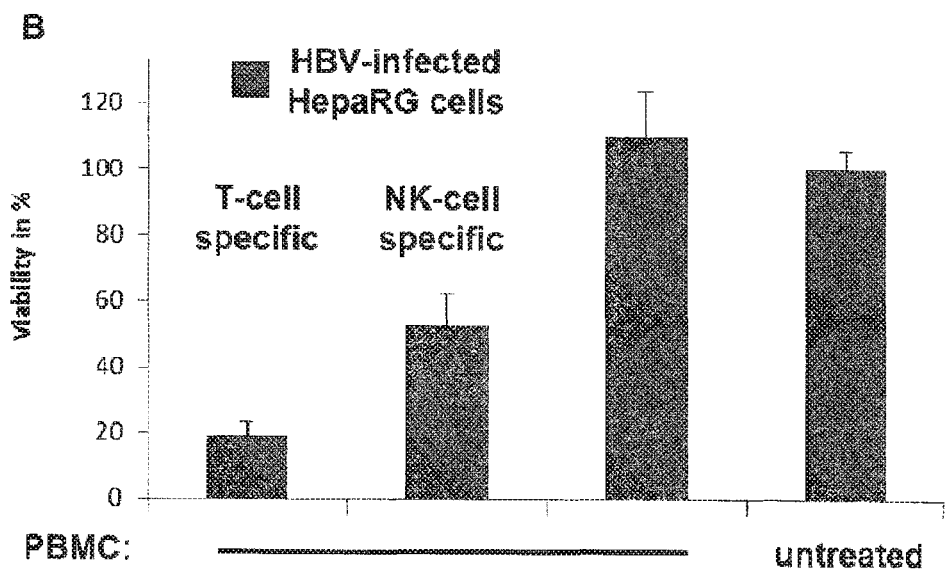

The combined use of bispecific molecules binding to two distinct CTL markers or NK markers has been found to provide for synergistic effects. FIGS. 3 and 4B show a comparison of specific target cell lysis upon administration of bispecific constructs.

In a particularly preferred embodiment, said two polypeptides comprise or consist of the sequences of (a) SEQ ID NOs: 43 and 44; or (b) SEQ ID NOs: 45 and 46.

Each of sequences SEQ ID NOs: 43 to 46 allows for the formation of two disulfide bridges when a homodimer is formed. Having said that, it is deliberately envisaged to form also heterodimers. An example of a heterodimer would be a covalently linked complex of two polypeptides of the present invention, wherein a first polypeptide would bind to a HBV surface antigen and a first marker presented by an immune effector cell and a second polypeptide would bind to an HBV surface antigen and a second marker of an immune effector cell. The two markers of an immune effector cell may be, for example, CD3 and CD28, or, in the alternative CD16 and CD56.

In a further aspect, the present invention provides a pharmaceutical composition comprising or consisting of one or more polypeptides of the invention, one or more complexes of the invention and/or one or more compositions of the invention.

The pharmaceutical composition may further comprise pharmaceutically acceptable carriers, excipients and/or diluents. Examples of suitable pharmaceutical carriers, excipients and/or diluents are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, subcutaneous or oral administration, these three options being preferred, and furthermore by intraperitoneal, intramuscular, topical, intradermal, intranasal or intrabronchial administration. Formulations for oral administration include tablets and syrups. It is particularly preferred that said administration is carried out by injection. The compositions may also be administered directly to the target site, e.g., by biolistic delivery to an external or internal target site. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Proteinaceous pharmaceutically active matter may be present in amounts between 1 ng and 10 mg/kg body weight per dose; however, doses below or above this exemplary range are envisioned, especially considering the aforementioned factors. If the regimen is a continuous infusion, it should also be in the range of 1 µg to 10 mg units per kilogram of body weight per minute.

Particularly preferred is intravenous administration.

In a further aspect, the present invention provides one or more polypeptides of any the invention, one or more complexes of the invention and/or one or more compositions of any one of the invention for use in a method of treating or preventing HBV infection and/or a condition caused by said HBV infection, said condition caused by said HBV infection being selected from liver cirrhosis, hepatocellular carcinoma, and liver cancer, said liver cancer being characterized by the expression of one or more HBV surface antigens. It is preferred that said hepatocellular carcinoma is characterized by the expression of one or more of the above defined HBV surface antigens.

In a further aspect, the present invention provides a method of treating or preventing HBV infection and/or a condition caused by said HBV infection, said condition caused by said HBV infection being selected from liver cirrhosis and hepatocellular carcinoma, said method comprising administering a therapeutically effective amount or a preventive amount, respectively, of one or more polypeptides of the invention, one or more complexes of the invention and/or one or more compositions of the invention to a patient in need thereof.

It is preferred that said pharmaceutical composition, said polypeptide/complex/composition for use in a method of treating and said method of treating, the recited polypeptides, complexes and/or compositions are the only pharmaceutically active agents comprised or used.

Having said that, it is also deliberately envisaged to incorporate one or more further pharmaceutically active agents in a combination therapy. Such further pharmaceutically active agents may be selected from interferons or other immunomodulators (such as e.g., interferon alpha 2a or 2b, interferon lambda), directly acting antivirals such as nucleos(t)ide analogues (such as e.g., Lamivudine (Epivir-HBV, Zeffix or Heptodin), Adefovir dipivoxil (Hepsera, Preveon), Entecavir (Baraclude, Entaliv), Telbivudine (Tyzeka, Sebivo), Tenofovir (Viread)), entry inhibitors (such as e.g., Myrcludex-B), other antivirals, or cytokines such as Interleukin-2.

In a further aspect, the present invention provides an in vitro method of killing cells infected with HBV, said method comprising culturing said cells infected with HBV with (i) immune effector cells and (ii) one or more polypeptides of the invention, one or more complexes of the invention and/or one or more compositions of the invention.

In a preferred embodiment of the in vitro method, said immune effector cells (i) are comprised in peripheral blood mononuclear cells; or (ii) are or comprise NK cells and/or CTLs.

In a further aspect, the present invention provides an in vitro or ex vivo Immune effector cell, which has a polypeptide of the invention or a complex in accordance with the invention bound to a surface antigen of said immune effector cell. Preferred immune effector cells and preferred surface antigens presented by immune effector cells are as defined above. Such immune effector cell is useful for administration to a patient suffering from HBV infection, liver cirrhosis or hepatocellular carcinoma. Accordingly provided is also a pharmaceutical composition comprising or consisting of an immune effector cell which has bound to a surface antigen thereof a polypeptide of the invention or a complex in accordance with the invention. Also provided is an immune effector cell which has bound to a surface antigen thereof a polypeptide of the invention or a complex in accordance with the invention for use in a method of treating or preventing HBV infection, liver cirrhosis or hepatocellular carcinoma.

Sequences disclosed in this application

```
SEQ ID NO 1
C8 HC CDR1
Gly Phe Thr Phe Ser Gly Tyr Ala

SEQ ID NO 2
C8 HC CDR2
Ile Ser Gly Ser Gly Gly Ser Thr

SEQ ID NO 3
C8 HC CDR3
Ala Lys Pro Pro Gly Arg Gln Glu Tyr Tyr Gly Ser Ser Ile Tyr Tyr Phe Pro Leu Gly
Asn

SEQ ID NO 4
C8 LC CDR1
Asn Ile Gly Ser Lys Ser

SEQ ID NO 5
C8 LC CDR2
Asp Asp Ser

SEQ ID NO 6
C8 LC CDR3
Gln Val Trp Asp Ser Ser Ser Asp Leu Val Val

SEQ ID NO 7
5F9 HC CDR1
Gly Phe Thr Phe Asn Asn Tyr Ala

SEQ ID NO 8
5F9 HC CDR2
Ile Asn Ser Asp Gly Arg Ser Thr

SEQ ID NO 9
5F9 HC CDR3
Ala Arg Thr Phe Tyr Ala Asp Tyr

SEQ ID NO 10
5F9 LC CDR1
Gln Asn Val Asp Thr Thr
```

```
SEQ ID NO 11
5F9 LC CDR2
Trp Ala Ser

SEQ ID NO 12
5F9 LC CDR3
Gln Gln Tyr Ser Ile Phe Pro Tyr Thr

SEQ ID NO 13
5A19 HC CDR1
Gly Phe Thr Phe Ser Ser Tyr Ala

SEQ ID NO 14
5A19 HC CDR2
Val Ser Ser Asp Gly Ser Tyr Ala

SEQ ID NO 15
5A19 HC CDR3
Ala Ser Phe Asn Trp Asp Val Ala Tyr

SEQ ID NO 16
5A19 LC CDR1
Gln Ser Leu Leu Asn Thr Arg Thr Arg Lys Ser Tyr

SEQ ID NO 17
5A19 LC CDR2
Trp Ala Ser

SEQ ID NO 18
5A19 LC CDR3
Lys Gln Ser Tyr Ser Leu Tyr Thr

SEQ ID NO 19
OKT3 HC CDR1
Gly Tyr Thr Phe Thr Arg Tyr Thr

SEQ ID NO 20
OKT3 HC CDR2
He Asn Pro Ser Arg Gly Tyr Thr

SEQ ID NO 21
OKT3 HC CDR3
Ala Arg Tyr Tyr Asp Asp His Tyr Cys Leu Asp Tyr

SEQ ID NO 22
OKT3 LC CDR1
Ser Ser Val Ser Tyr

SEQ ID NO 23
OKT3 LC CDR2
Asp Thr Ser

SEQ ID NO 24
OKT3 LC CDR3
Gln Gln Trp Ser Ser Asn Pro Phe Thr

SEQ ID NO 25
9.3 HC CDR1
Gly Phe Ser Leu Ser Asp Tyr Gly

SEQ ID NO 26
9.3 HC CDR2
Ile Trp Ala Gly Gly Gly Thr

SEQ ID NO 27
9.3 HC CDR3
Ala Arg Asp Lys Gly Tyr Ser Tyr Tyr Tyr Ser Met Asp Tyr

SEQ ID NO 28
9.3 LC CDR1
Glu Ser Val Glu Tyr Tyr Val Thr Ser Leu

SEQ ID NO 29
9.3 LC CDR2
Ala Ala Ser
```

SEQ ID NO 30
9.3 LC CDR3
Gln Gln Ser Arg Lys Val Pro Tyr Thr

SEQ ID NO 31
A9 HC CDR1
Gly Tyr Thr Phe Thr Asn Tyr Trp

SEQ ID NO 32
A9 HC CDR2
Ile Tyr Pro Gly Gly Gly Tyr Thr

SEQ ID NO 33
A9 HC CDR3
Ala Arg Ser Ala Ser Trp Tyr Phe Asp Val

SEQ ID NO 34
A9 LC CDR1
Thr Gly Thr Val Thr Thr Ser Asn Tyr

SEQ ID NO 35
A9 LC CDR2
His Thr Asn

SEQ ID NO 36
A9 LC CDR3
Ala Leu Trp Tyr Asn Asn His Trp Val

SEQ ID NO 37
NCAM29.2 HC CDR1
Gly Phe Thr Phe Ser Ser Phe Gly

SEQ ID NO 38
NCAM29.2 HC CDR2
Ile Ser Ser Gly Ser Tyr Ala Ile

SEQ ID NO 39
NCAM29.2 HC CDR3
Val Arg Gly Arg Arg Leu Gly Glu Gly Tyr Ala Met Asp Tyr

SEQ ID NO 40
NCAM29.2 LC CDR1
Gln Ser Leu Leu Tyr Ser Ser Asn Gln Lys Asn Tyr

SEQ ID NO 41
NCAM29.2 LC CDR2
Trp Ala Ser

SEQ ID NO 42
NCAM29.2 LC CDR3
Gln Gln Tyr Ser Ser Trp Thr

SEQ ID NO 43
C8-hIgG1Fc$_{mut}$-OKT3
MDFEVQIFSFLLISASVIMSRMAEVQLVESGGGLLQPGGSLRLSCAASGFTFSGYAMSWVRQA
PGKGLEWVSSISGSGGSTYYADSVKGRFTISRDNSKNTLYLQMNSLRAEDTALYYCAKPPGRQ
EYYGSSIYYFPLGNWGQGTLVTVSSASTKGPKLEEGEFSEARVQSALTQPASVSVAPGQTARI
TCGGNNIGSKSVHWYQQKPGQAPVLVVYDDSDRPSGIPERFSGSNSGNTATLTISRVEAGDEA
DYYCQVWDSSSDLVVFGGGTKLTVLGNSGGGGSGGGGSGGGGSASEPKSSDKTHTCPPCPAPP
AAGPSVFLFPPKPKDTLMISRTPEVTCVVVDVSHEDPEVKFNWYVDGVEVHNAKTKPREEQYN
STYRVVSVLTVLHQDWLNGKEYKCAVSNKGLASSIEKTISKAKGQPREPQVYTLPPSRDELTK
NQVSLTCLVKGFYPSDIAVEWESNGQPENNYKTTPPVLDSDGSFFLYSKLTVDKSRWQQGNVF
SCSVMHEALHNHYTQKSLSLSPGKDPGWSHPQFEKSRGGGGQVQLQQSGAELARPGASVKMSC
KASGYTFTRYTMHWVKQRPGQGLEWIGYINPSRGYTNYNQKFKDKATLTTDKSSSTAYMQLSS
LTSEDSAVYYCARYYDDHYCLDYWGQGTTLTVSSGNSGGGGSGGGGSGGGGSASQIVLTQSPA
IMSASPGEKVTMTCSASSSVSYMNWYQQKSGTSPKRWIYDTSKLASGVPAHRFGSGSGTSYSL
TISGMEAEDAATYYCQQWSSNPFTFGSGTKLEINGNS SEQ ID NO 44
C8-hIgG1Fc$_{mut}$-9.3
MDFEVQIFSFLLISASVIMSRMAEVQLVESGGGLLQPGGSLRLSCAASGFTFSGYAMSWVRQA
PGKGLEWVSSISGSGGSTYYADSVKGRFTISRDNSKNTLYLQMNSLRAEDTALYYCAKPPGRQ
EYYGSSIYYFPLGNWGQGTLVTVSSASTKGPKLEEGEFSEARVQSALTQPASVSVAPGQTARI
TCGGNNIGSKSVHWYQQKPGQAPVLVVYDDSDRPSGIPERFSGSNSGNTATLTISRVEAGDEA
DYYCQVWDSSSDLVVFGGGTKLTVLGNSGGGGSGGGGSGGGGSASEPKSSDKTHTCPPCPAPP
AAGPSVFLFPPKPKDTLMISRTPEVTCVVVDVSHEDPEVKFNWYVDGVEVHNAKTKPREEQYN
STYRVVSVLTVLHQDWLNGKEYKCAVSNKGLASSIEKTISKAKGQPREPQVYTLPPSRDELTK
NQVSLTCLVKGFYPSDIAVEWESNGQPENNYKTTPPVLDSDGSFFLYSKLTVDKSRWQQGNVF

```
SCSVMHEALHNHYTQKSLSLSPGKDPGWSHPQFEKSSGGGGQVQLQESGPGLVTPSQSLSITC
TVSGFSLSDYGVHWVRQSPGQGLEWLGVIWAGGGTNYNSALMSRKSISKDNSKSQVFLKMNSL
QADDTAVYYCARDKGYSYYYSMDYWGQGTTVTVSSRGGGSGGGGSGGGGSDIELTQSPASLAV
SLGQRATISCRASESVEYYVTSLMQWYQQKPGQPPKLLIFAASNVESGVPARFSGSGSGTNFS
LNIHPVDEDDVAMYFCQQSRKVPYTFGGGTKLEIKR

SEQ ID NO 45
C8-hIgG1Fc_mut-A9
MDFEVQIFSFLLISASVIMSRMAEVQLVESGGGLLQPGGSLRLSCAASGFTFSGYAMSWVRQA
PGKGLEWVSSISGSGGSTYYADSVKGRFTISRDNSKNTLYLQMNSLRAEDTALYYCAKPPGRQ
EYYGSSIYYFPLGNWGQGTLVTVSSASTKGPKLEEGEFSEARVQSALTQPASVSVAPGQTARI
TCGGNNIGSKSVHWYQQKPGQAPVLVVYDDSDRPSGIPERFSGSNSGNTATLTISRVEAGDEA
DYYCQVWDSSSDLVVFGGGTKLTVLGNSGGGGSGGGGSGGGGSASEPKSSDKTHTCPPCPAPP
AAGPSVFLFPPKPKDTLMISRTPEVTCVVVDVSHEDPEVKFNWYVDGVEVHNAKTKPREEQYN
STYRVVSVLTVLHQDWLNGKEYKCAVSNKGLASSIEKTISKAKGQPREPQVYTLPPSRDELTK
NQVSLTCLVKGFYPSDIAVEWESNGQPENNYKTTPPVLDSDGSFFLYSKLTVDKSRWQQGNVF
SCSVMHEALHNHYTQKSLSLSPGKDPGWSHPQFEKSRGGGGQVQLQQSGAELVRPGTSVKISC
KASGYTFTNYWLGWVKQRPGHGLEWIGDIYPGGGYTNYNEKFKGKATVTADTSSRTAYVQVRS
LTSEDSAVYFCARSASWYFDVWGAGTTVTVSSGNSGGGGSGGGGSGGGGSASQAVVTQESALT
TSPGETVTLTCRSNTGTVTTSNYANWVQEKPDHLFTGLIGHTNNRAPGVPARFSGSLIGDKAA
LTITGAQTEDEAIYFCALWYNNHWVFGGGTKLTVL SEQ ID NO 46
C8-hIgG1Fc_mut-NCAM29.2
MDFEVQIFSFLLISASVIMSRMAEVQLVESGGGLLQPGGSLRLSCAASGFTFSGYAMSWVRQA
PGKGLEWVSSISGSGGSTYYADSVKGRFTISRDNSKNTLYLQMNSLRAEDTALYYCAKPPGRQ
EYYGSSIYYFPLGNWGQGTLVTVSSASTKGPKLEEGEFSEARVQSALTQPASVSVAPGQTARI
TGGGNNIGSKSVHWYQQKPGQAPVLVVYDDSDRPSGIPERFSGSNSGNTATLTISRVEAGDEA
DYYCQVWDSSSDLVVFGGGTKLTVLGNSGGGGSGGGGSGGGGSASEPKSSDKTHTCPPCPAPP
AAGPSVFLFPPKPKDTLMISRTPEVTCVVVDVSHEDPEVKFNWYVDGVEVHNAKTKPREEQYN
STYRVVSVLTVLHQDWLNGKEYKCAVSNKGLASSIEKTISKAKGQPREPQVYTLPPSRDELTK
NQVSLTCLVKGFYPSDIAVEWESNGQPENNYKTTPPVLDSDGSFFLYSKLTVDKSRWQQGNVF
SCSVMHEALHNHYTQKSLSLSPGKDPGWSHPQFEKSGGGGDVQLVESGGGLVQPGGSRKLSCA
ASGFTFSSFGMHWVRQAPEKGLEWVAYISSGSYAIYYADTVKGRFTISRDNPENTLFLQMTSL
RSEDSAMYYCVRGRRLGEGYAMDYWGQGTSVTVSSGNSGGGGSGGGGSGGGGSASDIVMSQSP
SSLAVSVGEKVTMSCKSSQSLLYSSNQKNYLAWYQQKPGQSPKLLIYWASTRKSGVPDRFTGS
GSGTDFTLTISSVKAEDLAVYYCQQYSSWTFGGGTKLEIKR SEQ ID NO 47
Gly Gly Gly Gly Ser Gly Gly Gly Gly Ser Gly Gly Gly Gly Ser SEQ ID NO 48
Ala Lys Thr Thr Pro Lys Leu Glu Glu Gly Glu Phe Ser Glu Ala Arg Val SEQ ID NO 49
Gly Gly Gly Gly Ser Gly Gly Gly Gly Ser Gly Gly Gly Gly Ser Gly Gly Gly Gly Ser
```

The figures illustrate the invention.

FIG. 1:

scFv fragments are obtained by fusion of two variable domains. Fusion involves the use of a flexible peptide linker which does not or not substantially interfere with the structure of each variable domain.

FIG. 2:

Dimerization of two polypeptides of the invention by the formation of disulfide bonds. Each polypeptide comprises a bispecific bivalent antibody. Natural antibody dimerization in the endoplasmic reticulum of producer cells can result in formation of a bispecific tetravalent antibody, or a tri- or tetraspecific, tetravalent antibody if two bispecific bivalent antibodies are co-expressed (not shown).

FIG. 3:

Comparison of specific elimination of HBV surface antigen producing hepatoma target cells after administration of single bispecific antibodies and synergistic effects of simultaneous administration of two CTL-specific or two NK cell-specific bispecific antibodies. The CellTiter-Blue Cell Viability Assay is used.

FIG. 4:

A) Cytokine secretion as an indication of activation of immune effector cells in the presence of bispecific antibodies of the present invention. HBV-infected HepaRG cells were co-cultured with PBMC in the presence or absence of indicated bispecific antibodies.

B) Specific elimination of HBV-infected target cells in co-culture with immune effector cells and bispecific antibodies.

FIG. 5:

Viability of target cells co-cultured with PBMC In presence of Individual HBs-reactive bispecific antibodies. Single bispecific antibodies mediate lysis of target cells. A, C, E: Effect of stimulation with αHBsxαCD3 (A), αHBsxαCD28 (C) or summarized (E). B, D, F: Effect of stimulation with αHBsxαCD3 [FcΔADCC] (B), αHBsxαCD28 [FcΔADCC] (D) or summarized (F). The arrowhead indicates addition of PBMC and bispecific antibodies. Curves with dots represent HBs-transfected HuH7-S cells, curves with rhombuses represent HuH7 parental hepatoma cells. The xCELUgence real-time cytotoxicity assay is used. Normalization time of cell index: 0 h.

FIG. 6:

Viability of target cells co-cultured with PBMC in presence of HBs-reactive bispecific antibodies. Combination of bispecific antibodies mediate massive killing of target cells. A: Effect of stimulation with αHBsxαCD3 and αHBsxαCD28. B: Effect of stimulation with αHBsxαCD3 [FcΔADCC] and αHBsxαCD28 [FcΔADCC]. C, D: Effect of individual bispecific antibodies compared to combinations. The arrowhead indicates addition of PBMC and bispecific antibodies. Curves with dots represent HuH7-S cells, curves with rhombuses HuH7 cells. Normalization time of cell index: 0 h.

FIG. 7:

Viability of target cells co-cultured with PBMCs in the presence of different concentrations of bispecific antibodies. 50 µl/50 µl mixtures of antibody-containing supernatants of αHBsxαCD3/αHBsxαCD28 (A), or αHBsxαCD3 [FcΔADCC]/αHBsxαCD28 [FcΔADCC] (B), induced lysis of target cells earlier than 25 µl/25 µl mixtures, indicating dose-dependent effects. The arrowhead indicates addition of PBMCs and bispecific antibodies. Curves with dots represent HuH7-S cells, curves with rhombuses HuH7 cells. Normalization time of cell index: 0 h.

FIG. 8:

Viability of target cells co-cultured with different amounts of PBMC in the presence of a mixture of αHBsxαCD3 and αHBsxαCD28. $2\times10^5$ PBMC mediate a significantly earlier elimination of HuH7-S cells than $1\times10^5$ PBMC. The arrowhead indicates addition of PBMC and bispecific antibodies. Curves with dots represent HuH7-S cells, curves with rhombuses HuH7 cells. Normalization time of cell index: 0 h.

FIG. 9:

Viability of target cells co-cultured with PBMCs in presence of αHBsxαCD3/αHBsxαCD28 mixtures for various time periods. Supernatants containing bispecific antibodies were removed after the indicated periods of stimulation. 4 h stimulation only led to a small decrease of target cell viability (78.5% endpoint viability). Stimulation of PBMC with bispecific antibodies for 8 h or longer induced elimination of target cells. After stimulation for 8 h and 12 h, killing of target cells was delayed as compared to 24 h or 48 h stimulation, suggesting continuous activation and re-targeting of effector cells. HuH7-S endpoint viabilities at 48 h were, however, comparable: 8 h stim.: 14.7%; 12 h stim.: 11.7%, 24 h stim.: 5.1%, 48 h stim.: 3.2%). The arrowhead indicates addition of PBMC and bispecific constructs. Viability kinetics for HuH7-S cells are shown. Normalization time of cell index: 0 h.

FIG. 10:

IL-2, IFN-γ and TNF-α secretion of PBMC after co-culture with HuH7-S/HuH7 cells in presence of αHBsxαCD3/αHBsxαCD28 at different time points. A: IL-2 concentration increased over time and reached a plateau at approximately 24 h with a concentration of about 1550 pg/ml. B: IFN-γ secretion started between 8 h and 12 h and increased up to 12000 pg/ml (48 h). C: TNF-α production was detectable already after 4 h, increased continuously, reached its peak at 24 h (1700 pg/ml) and declined to 1400 pg/ml after 48 h. High background TNF-α secretion in the absence of HBs (HuH7 cells) could be detected, with the highest concentration after 4 h (~70 pg/ml) decreasing to 9 pg/ml after 48 h of co-culture.

FIG. 11:

LAMP-1 stainings after co-culture of PBMC with HuH7-S/HuH7 cells in presence of bispecific antibodies. Surface expression of the endosomal degranulation marker LAMP-1 is detected on $CD4^+$ (A, B) and $CD8^+$ (C, D) T cells after co-culture with HuH7-S (black line) or HuH7 (grey line) cells in the presence of either αHBsxαCD3/αHBsxαCD28 (A, C) or αHBsxαCD3 [FcΔADCC]/αHBsxαCD28 [FcΔADCC]. (B, D).

FIG. 12:

FACS analysis of PBMC co-cultured with HuH7-S or HuH7 cells in the presence of αHBsxαCD3/αHBsxαCD28 after 8 h, 12 h and 24 h. A, B; Percentages of $IFN\gamma^+/IL-2^+/TNF\alpha^+/CD154^+$ $CD4^+$ T cells (A) or $IFN\gamma^+/IL-2^+/TNF\alpha^+/CD154^+$ $CD8^+$ (B) T cells. C, D: Boolean combination gates of $IFN\gamma^+$, $IL-2^+$ and/or $TNF\alpha^+$ $CD4^+$ (C), or $IFN\gamma^+$, $IL-2^+$ and/or $TNF\alpha^+$ $CD8^+$ (D) T cells.

FIG. 13:

FACS analysis of PBMC co-cultured with immobilized or soluble HBsAg in the presence of αHBsxαCD3 [FcΔADCC]/αHBsxαCD28 [FcΔADCC] after 24 h and 48 h. A, B; Percentages of $IFN\gamma^+/IL-2^+/TNF\alpha^+/CD154^+$ $CD4^+$ T cells (A) or $IFN\gamma/IL-2^+/TNF\alpha^+/CD154^+$ $CD8^+$ (B) T cells. C, D: Boolean combination gates of $IFN\gamma^+$, $IL-2^+$ and/or $TNF\alpha^+$ CD4 (C), or $IFN\gamma$, $IL-2^+$ and/or $TNF\alpha^+$ $CD8^+$ (D) T cells.

FIG. 14:

HBsAg in the supernatant of HuH7-S cells (110.8 S/CO), HepG2.2.15 cells (41.7 S/CO) and HBV-infected HepaRG cells (16.5 S/CO).

FIG. 15:

Viability of HBV-infected/uninfected HepaRG cells co-cultured with PBMC in presence of bispecific antibodies. αHBsxαCD3 (A) and αHBsxαCD3/αHBsxαCD28 (B) mediate significant target cell lysis. Endpoint viabilities of untreated cells are 65.9% (HBV+) and 62.9% (HBV−). The arrowhead indicates addition of PBMCs and bispecific constructs. Curves with dots represent HBV-infected HepaRG cells, curves with rhombuses uninfected HepaRG cells. Normalization time of cell index in xCELLigence assay: 0 h.

FIG. 16:

Reduction in tumor size in animal treated with bispecific antibodies. Mice bearing HBV-positive subcutaneous HepG2.2.15 tumors were treated with human PBMC and a mixture of αHBsxαCD3 and αHBsxαCD28 bispecific antibodies at four consecutive days. Mice were sacrificed and tumor size was analyzed.

The examples illustrate the invention.

EXAMPLE 1

Materials and Methods for Example 2

Cloning and Production of Bispecific Antibodies

Complementary DNAs coding for variable heavy and variable light chains of anti-CD3 (OKT3), anti-CD28 (9.3), anti-CD18 (A9) and anti-CD56 (NCAM29.2) were obtained by PCR amplification of reverse-transcribed mRNAs from the respective hybridoma using a set of primers covering all $V_H$ and Vκ/Vλ subtypes. PCR products were ligated into pCR2.1-TOPO (Invitrogen, Life Technologies) and sequenced. The anti-HBsAg scFv C8 was provided in a codon-optimized form in the plasmid pMP71-C8. Using primers containing appropriate restriction sites in the 5' and 3' flanks variable heavy and variable light chain cDNAs coding for the above mentioned antibodies were assembled with a glycine-serine linker into scFvs. The OKT3, 9.3, A9, and NCAM29.2 scFvs (N-terminally extended by $(Gly)_{3-4}$) were cloned at the 3' end of a cDNA present in pBluescript KS II+ (Stratagene) that codes for the Fc domain (hinge, CH2, CH3) of human IgG1 which was extended by glycine-serine linker GlyAsnSer(Gly$_4$Ser)$_3$AlaSer at the 5' end and a StrepTag sequence (WSHPQFEK) and, in a second series of constructs, an additional glycine-serine linker (Gly$_4$Ser)$_3$ at the 3' end. The C8 scFv coding sequence was cloned at the 5' end of the mentioned 5' glycine-serine linker. The complete scFv-linker-hIgG1Fc-linker-scFv sequence was subcloned into the mammalian expression vector pcDNA3.1(−)

(Invitrogen). Maxi-prep plasmid DNA was used for transfection of HEK293 cells using the peqFECT transfection reagent (Peqab). Stable transfectants were selected using 0.8-1.0 mg/ml G418 and expanded. Supernatants from HEK transfectants were collected and analyzed by ELISA for the concentration of secreted, bispecific antibodies and by Western blot for the integrity of the secreted antibodies using goat anti-human IgG-Fc specific, peroxidase-labeled antibodies.

Cell Culture Conditions and HBV Infection

HuH7 hepatoma cells (Nakabayaski, et al. 1982. Growth of human hepatoma cell lines with differentiated functions in chemically defined medium. Cancer Res. 42: 3858-3863) and HEK293 cells were maintained in Dulbecco's modified Eagle medium (DMEM) supplemented with 10% fetal bovine serum (FBS), penicillin (100 U/mL), streptomycin (100 µg/mL), and L-glutamine (2 mmol/L) (all from GIBCO, Life Technologies).

Peripheral blood mononuclear cells (PBMC) were isolated through density gradient centrifugation from heparinized whole blood using LSM 1077 Lymphocyte Separation Medium (PAA). 25 ml of blood was layered above 13 ml of LSM 1077. After centrifugation at 2000 rpm for 20 min (without break) at room temperature PBMC were harvested and cultured in RPMI 1640 medium supplemented with 10% fetal bovine serum (FBS), penicillin (100 U/mL), streptomycin (100 µg/ml), and L-glutamine (2 mmol/l) (all from GIBCO). After an overnight resting step PBMC or sorted NK cells were used for co-culture experiments.

HepaRG cells were maintained in Williams E Medium (Invitrogen GmbH, Karlsruhe, Germany) supplemented with L-glutamine (5 mmol/l), glucose (0.06% [wt/vol]), HEPES (23 mmol/l, pH7.4), gentamycin (50 µg/ml), penicillin (501 U/ml), streptomycin (50 µg/ml), inosine (37 µmol/l), hydrocortisone (4.8 µg/ml), and insulin (1 µg/ml). Prior to infection HepaRG cells were differentiated for 4 weeks using differentiation medium (Williams E Medium (as described above), supplemented with DMSO (1.75%). HepaRG cells were Infected using HBV stocks at a final m.o.i. of 200 and PEG (5%) in differentiation medium. Infection inoculum was removed after overnight incubation and replaced with differentiation medium and cultured for 6 days.

For co-cultures with redirected T cells, we changed from differentiation medium to hydrocortison-free medium 2 days before starting the co-culture to avoid immunosuppression mediated by the hydrocortison.

Transfection with HBV Surface Antigen Encoding Plasmids

HuH-7 cells were transfected with plasmids encoding the various surface antigens using FuGene transfection reagent (Promega). For 8 wells of a 96 well plate 3 µl of FuGENE, 1 µg of plasmid DNA were added to 100 µl OptiMEM (Gibco). The transfection solution was Incubated for 15 min at room temperature in order for the FuGENE to bind the plasmid DNA. A final volume of 100 µl was applied per well, after adding further OptiMEM and incubated for at least 24 h.

Magnetic Activated Cell Sorting (MACS) of NK Cells

NK cells were isolated from PBMC using a human CD56$^+$CD16$^+$ NK Cell Isolation Kit (Miltenyi) In a first negative selection step, all non-NK cells were removed by monoclonal antibodies directed against antigens not expressed on the surface of NK cells. In a second positive selection step, the NK cells were isolated by monoclonal CD16 antibodies conjugated to iron oxide microbeads and retained inside a magnetic field. After isolation NK cells were cultured in RPMI-1640 medium as described above.

Co-Culture of HBV-Positive Target Cells and Redirected Effector Cells

Target cells were cultured in a 96 well plate at full confluency. $1 \times 10^5$ effector cells were added in a volume of 100 µl medium per well. 100 µl of the HEK supernatants containing the bispecific antibodies were applied per well. For determination of synergistic effects, 50 µl of each bispecific antibody supernatant was added per well. Untreated target cells incubated with 200 µl medium or with effector cells alone or with bispecific antibodies alone served as negative control.

Enzyme-Linked Immunosorbent Assay (ELISA) for Effector Cell Activation

Cytokine secretion resulting from activation of effector cells was detected by ELISA. Using the Human IFN-γ ELISA MAX™ (BioLegend). The absorbance at 450 nm was detected using the program Magellan6 and an InfiniteF200 (Tecan).

Target Cell Viability Assay

The target cell viability after co-culture was determined using the CellTiter-Blue Cell Viability Assay (Promega). This assay is based on the ability of living cells to convert a redox dye (resazurin) into a fluorescent end product (resorufin) due to metabolic activity. Nonviable cells rapidly lose their metabolic capacity and thus do not generate a fluorescent signal. After removal of the supernatant 100 µl of colorless DMEM containing 20% CellTiter-Blue Reagent was added per well to the co-cultures and incubated at 37° C. for 2 hours. The fluorescence signal was recorded at 560 nm using an InfiniteF200 (Tecan).

EXAMPLE 2

Results

In a first line of experiments we have evaluated the activity of the bispecific antibody constructs directed against CTL surface antigens CD3 and CD28 and against NK cell surface antigens CD16 and CD56. We employed plasmid-transfected hepatoma cell lines producing HBV surface antigens. After establishing the HBV protein expression, these target cells were co-cultured together with immune effector cells, namely PBMC and isolated NK cells, and bispecific antibody constructs. PBMC contain around 70% T cells but only 7% NK-cells. Therefore, we magnetically isolated CD16$^+$ CD56$^+$ NK cells. As negative controls we analyzed co-cultures with HBV-negative target cells, which had been preincubated with HBV− and subviral particle-containing supernatants. This control was employed to rule out activation of effector cells due to unspecific binding of HBV particles on the surface of HBV-negative target cells. Furthermore, we co-cultured HBV-positive target cells with immune effector cells in the absence of bispecific constructs to evaluate unspecific background cytotoxicity. To exclude a cytotoxic effect of the bispecific constructs, we prepared cultures of HBV-positive target cells without immune effector cells in the presence of bispecific constructs.

These experiments showed a specific activation of CTLs upon co-culture in the presence of the CD3- or CD28-specific constructs as determined by the secretion of the proinflammatory cytokine interferon gamma (IFNγ) of up to 7000 pg/ml. This effect was further enhanced upon co-administration of CD3- and CD28-specific constructs demonstrating a synergistic effect.

Furthermore, the bispecific constructs mediated a specific cytotoxic elimination of HBsAg-producing HuH7 hepatoma cell lines (FIG. 3) of up to 90% reductions of target cell viability in comparison to controls. This cytotoxic response was observed for co-cultures of PBMC and HBV-positive target cells together with the bispecific constructs directed against CD3 and CD28 as well as for isolated NK-cells with constructs directed against CD16 and CD56. The co-administration of CTL- and NK-cell specific constructs further increased the cytotoxic effect synergistically to elimination rates above 95%. We observed unspecific background cytotoxicity of 15% to 40% for CTLs and NK cells, respectively.

In a second round of experiments we employed HBV-infected HepaRG hepatoma cells. This cell line allows for infection with HBV after a four week differentiation and mirrors the natural situation of HBV-infected tissues. Typically, Infection rates of HepaRG cells never reach 100% and this mixture of infected and non-infected cells mimics the situation in an HBV-infected individual under antiviral therapy, harboring both, infected and non-infected cells in the presence of free extracellular viral particles.

In co-cultures of immune effector cells and co-administered bispecific constructs, the HBV infected HepaRG cells mediated an efficient activation of both, CTLs and NK cells, with impressing amounts of IFN-γ secretion of up 60,000 pg/ml (FIG. 4A). In this experiment we did not isolate or enrich NK cells prior to co-culture.

Furthermore the bispecific antibody constructs resulted in a cytotoxic response of the activated immune effector cells leading to the specific elimination of HBV-infected target cells (FIG. 4B). We observed elimination rates of 50% to 70% for NK-cells and CTLs, respectively. Unspecific background cytotoxicity was absent in these experiments.

EXAMPLE 3

Methods for Example 4

To analyze the therapeutic potential of bispecific antibody constructs to successfully retarget T cells towards HBV-positive cells, in vitro co-culturing experiments were performed and analyzed in detail. We employed bispecific antibody constructs containing single chain binding domains directed against human CD3 (αCD3) and human CD28 (αCD28) and additionally, constructs containing directed mutations in their Fc spacer domain which should abrogate antibody dependent cellular cytotoxicity (ΔADCC), by circumventing Fcγ receptor binding. These were constructed as a safety measure to rule out unspecific activation of natural killer cells. On the other side, all bispecific antibody constructs harbored the HBV S-protein (HBsAg) specific binding domain C8. Peripheral blood mononucleated cells (PBMC) isolated from fresh venous blood of healthy donors were co-cultured with different human hepatoma cell lines as surrogate models for HBV-infection. We employed HuH7-S(HBV S-antigen transgenic) and as negative control the mother cell line HuH7 and HBV-infected or as control uninfected HepaRG cells. HepG2.2.15 (HBV genome transgenic) cell were used as controls for HBV- marker quantification. To provide bispecific antibody constructs, supernatant of producer cell lines containing bispecific antibodies was added. To visualize changes in target cell viability due to cytotoxicity mediated by bispecific antibodies over time, the xCELLigence system was employed. This technique allows for real-time monitoring of cell-viability over long time cultures. Therefore, target hepatoma cells were seeded on specially designed microtiter plates, which contain inter-digitated gold microelectrodes to noninvasively monitor the viability of adherent target cells using electrical impedance as a readout. The cytotoxic elimination results in a change of the impedance, which can be converted into the so called cell index (CI) value, which is used to monitor cell viability.

Co-Culturing with Target Cells

At day zero, $3 \times 10^4$ HuH7-S/HuH7 cells were seeded per well in a 96-well plate (E-Plate 96). At day 1, the supernatant was removed and $1 \times 10^5$ primary human PBMC in 100 μl PBMC medium or only 100 μl medium for controls were added to the respective wells. Additionally, 100 μl of supernatant containing bispecific antibodies, singly or in combinations were added. As negative control, 100 μl DMEM medium were added to the wells, resulting in a total volume of 200 μl. Co-cultures were monitored for 48 h or 72 h in the xCELLigence system.

HepaRG cells were grown to confluence, differentiated for 21 days and infected with HBV prior to immunotherapeutic experiments.

For the infection of HepaRG cells a virus stock was prepared in differentiation medium containing PEG and 50 μl were added per well. The final concentration of PEG was 5% and the MOI of the virus stock was set to 200 ($7.5 \times 10^6$ virus particles/well). 16 h after addition of the infection master mix, cells were washed 3 times with PBS to remove residual virus. Differentiation medium was added, and medium was changed every 3 days for a total of 12 days. Before co-culturing experiments, medium was changed to co-culturing medium (depleted of the immunosuppressant hydrocortisone). Successful HBV infection of HepaRG cells was tested by measuring HBsAg (Axsym) and HBeAg (BEP III System) in the supernatant of infected cells.

PBMC Preparation

PBMC for co-culturing experiments were isolated from whole blood. Heparinized fresh blood was diluted 1:1 with RPMI wash-medium. 25 ml of diluted blood was over layered onto 15 ml Percoll and centrifuged at 960 g for 20 min without break in a swing-out centrifuge. The PBMC were isolated and transferred into 50 ml with RPMI medium. After washing, cells were resuspended in 10 ml PBMC medium and cell number was determined. The concentration was adjusted to $2 \times 10^6$ cells/ml to ensure optimal conditions. PBMC were rested overnight at 37° C.

Fluorescence Activated Cell Sorting (FACS)

To examine effector functions of redirected PBMCs, FACS analysis was performed. Thereby, the secretion of the pro-inflammatory cytokines IFN-γ, IL-2 and TNF-α, as well as the expression of the activation marker CD154 (CD40L) and the degranulation marker LAMP-1 (CD107a), respectively, where analyzed. The measurement of cytokine production was performed using intracellular cytokine staining. Therefore 0.2 μg/ml Brefeldin A (BFA) was applied to cells and incubated for 4 hours at 37° C.

BFA blocks the forward transport between the endoplasmic reticulum and the Golgi apparatus and, as a consequence, exocytosis of cytokines is inhibited. In the case of simultaneous staining for LAMP-1, antibody was applied 1 h before adding BFA (to enable translocation of LAMP-1 to the cellular surface). Subsequently, cells were transferred to a 96-well plate (round bottom) and washed twice in 200 μl FACS buffer. For staining of viable cells and exclusion of dead cells, the LIVE/DEAD Fixable Near-IR Dead Cell Stain Kit was used. For fixation and permeabilization cells were resuspended in 100 μl Cytofix/Cytoperm reagent and incubated on ice in the dark for 20 min. After washing, cells were resuspended in the prepared antibody mix or only stained with the respective single colors for systematic compensation. Staining took place on ice in the dark for 30 min. After washing, cells were resuspended in 200 μl FACS buffer and transferred into FACS tubes for acquisition.

Acquisition was performed using either a FACSCanto II or LSR Fortessa. FACS Diva software was used to record data, analysis was performed using FlowJo software.

Animal Experiments

For a first test of bispecific constructs in vivo, experiments with immunodeficient Rag2/IL2Rγnull-mice (international nomenclature: B10;B6-Rag2tm1Fwa Il2rgtm1Wjl) were conducted. We injected 6 weeks old mice with $5 \times 10^8$ cells of the HBV-transgenic human hepatoma cell line HepG2.2.15. Cells were injected subcutaneously into the flank of the animals. This resulted in tumor formation over a 14 day time period. HBV replication inside the tumor was monitored through determination of HBV viremia. Human PBMC were isolated from fresh human cord blood and stimulated on plates precoated with antibodies against human CD3 and CD28 at a cell concentration of $0.25 \times 10^6$ PBMC per ml for 3 days. Subsequently cells were maintained in cell culture medium containing 300 U/ml of IL-2 for 7 days.

On day 14 after tumor induction, mice were injected with $2 \times 10^7$ PBMCs per mouse intraperitoneally and received 100 µl of αCD3/αCD28 bispecific antibody constructs in supernatant of HEK producer cells into the tail vein per animal at four consecutive days. Mice were sacrificed on day 18 after tumor induction and analysed for tumor size. Subsequently, serum and tissue samples were stored for further analyses.

EXAMPLE 4

Bispecific Antibodies Mediate Specific Elimination of HBV Surface Protein Expressing Target Cells (HuH7-S)

To examine whether bispecific antibody constructs successfully retarget T cells towards HBsAg expressing target cells and induce target cell lysis, isolated PBMC were co-cultured with HuH7-S cells in the presence of bispecific antibody constructs. HuH7-S cells were stably transfected to express HBsAg and therefore mimicked HBV-infected hepatocytes. This results in the production and secretion of subviral particles into the supernatant and the incorporation of HBsAg into the cellular membrane. Untransfected HuH7 cells served as negative control.

Individual Bispecific Antibodies Provoke Killing of Target Cells

Figure 5:
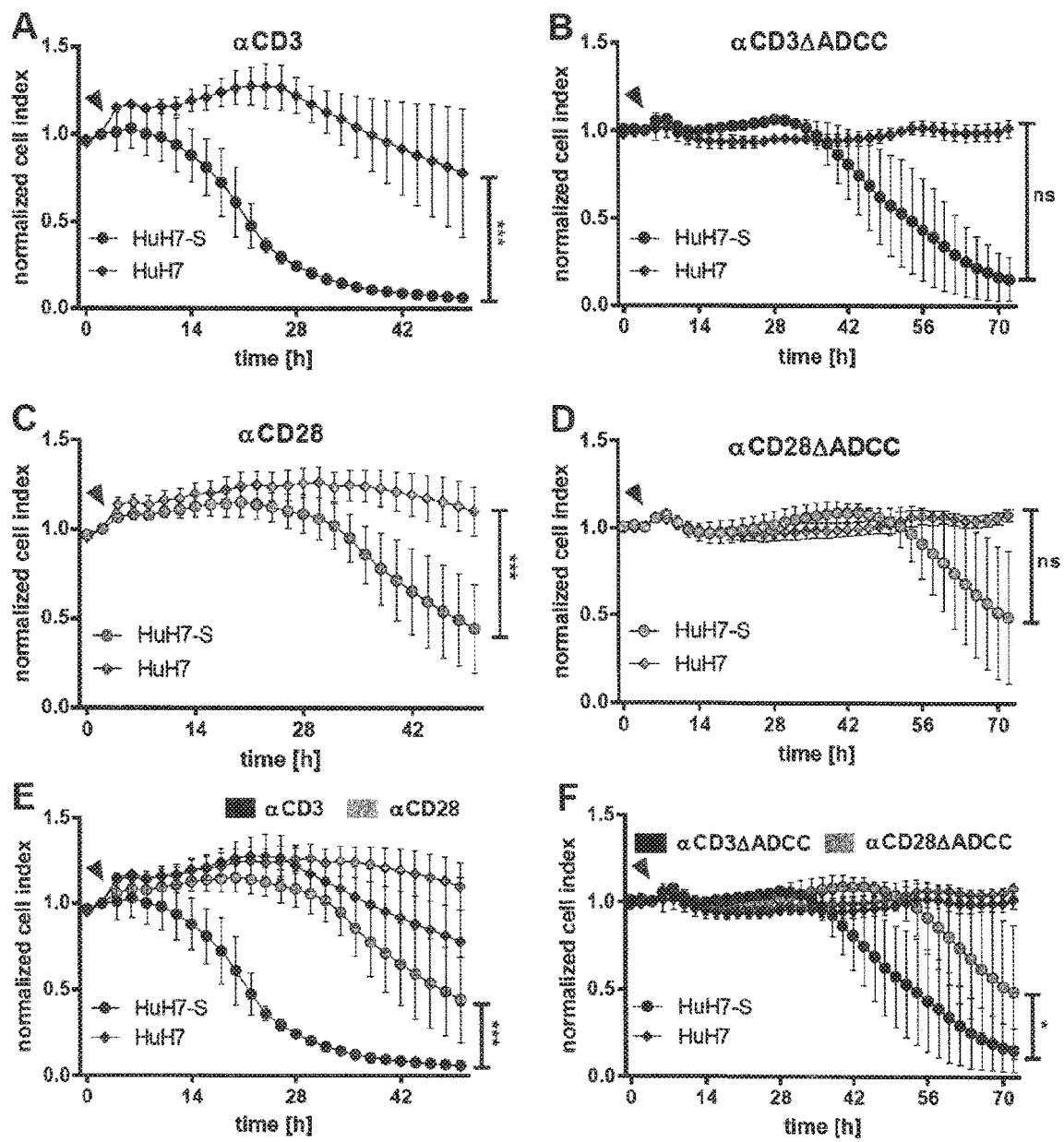

To analyze if the individual bispecific antibodies are able to stimulate T cell activation and mediate target cell lysis, PBMCs were co-cultured with HuH7-S/HuH7 cells in the presence of αHBsxαCD3, αHBsxαCD28, αHBsxαCD3 [FcΔADCC] or αHBsxαCD28 [FcΔADCC] bispecific tetravalent antibodies. The stimulation of effector cells by the single bispecific antibodies resulted in specific killing of HBsAg expressing target cells (FIG. 5). Bispecific antibodies directed against CD3 mediated elimination of target cells earlier and stronger than constructs directed against CD28, as the endpoint viability of HuH7-S cells treated with αCD3 only accounted for 6.4% (αCD3ΔADCC: 15.5%) compared to 44.42% for αCD28 (αCD28ΔADCC: 48.9%). Furthermore αCD3ΔADCC and αCD28ΔADCC required more time to induce lysis of target cells compared to αCD3 and αCD28, respectively. αCD3ΔADCC-mediated killing started approximately 35 h after starting the co-culture, whereas αCD3 led to a decrease of target cell viability already after 12 h. A time shift of about 20 h could also be observed between αCD28ΔADCC and αCD28-mediated target cell lysis. The stimulation with αCD3 also led to detectable lysis of HBsAg-negative HuH7 cells with an endpoint viability of 78.1%, Indicating unspecific activation. The same was true for stimulation with αCD3ΔADCC in some experiments even if not seen here. The viability of HuH7 cells during co-culture in presence of the other bispecific constructs remained at 100%.

This data demonstrates that stimulation with each of the individual bispecific antibodies provokes elimination of target cells without further co-stimulation.

Bispecific Antibodies Mediate Target Cell Lysis in a Synergistic Manner

Figure 6:
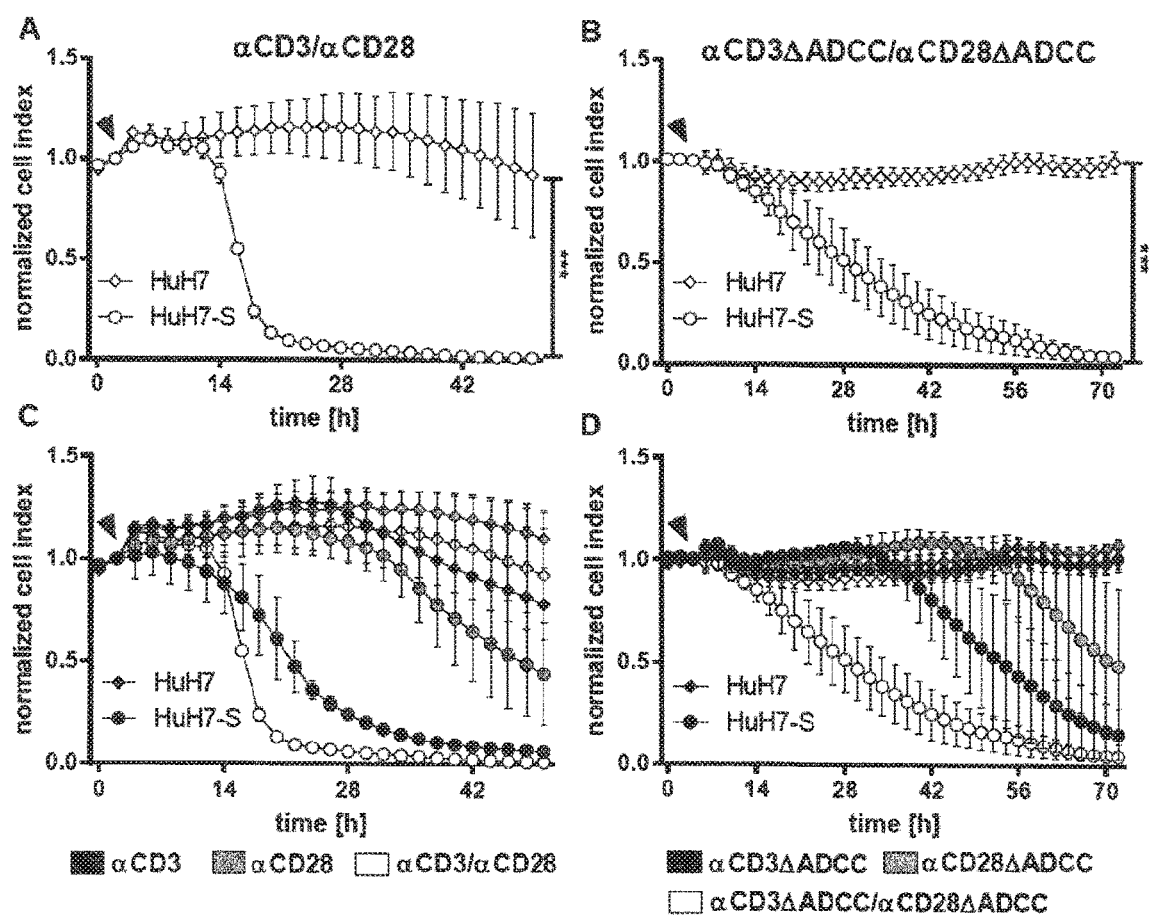

To further analyze whether combination of bispecific constructs leads to an enhanced activity and therefore cytotoxicity of effector cells, PBMCs were co-cultured with HuH7-S/HuH7 cells either in presence of the combinations of αCD3/αCD28 or αCD3ΔADCC/αCD28ΔADCC. As shown in FIG. 6, the combination of bispecific constructs led to massive killing of HBsAg expressing target cells with a remaining viability of 1.2% (αCD3/αCD28) and 4.4% (αCD3ΔADCC/αCD28ΔADCC), whereas nearly no HuH7 cells were eliminated (endpoint viability of HuH7 cells: αCD3/αCD28: 92.4%; αCD3ΔADCC/αCD28ΔADCC: 100.4%).

Again αCD3/αCD28-mediated lysis of target cells was faster than the killing induced by constructs with mutated Fc region, even if killing of target cells started at approximately the same time after about 11 h (FIG. 6A, B). Combination of bispecific antibodies led to a faster elimination of target cells compared to lysis induced by individual bispecific constructs (FIG. 6C, D). This was expected, as T cells receive not only one signal as in the presence of individual constructs, but obtain both, activation and co-stimulatory signal if an antibodies directed against CD3 and CD28 are present.

Thus, combination of bispecific constructs mediate specific lysis of HBV surface protein expressing target cells in a synergistic manner.

Figure 7:
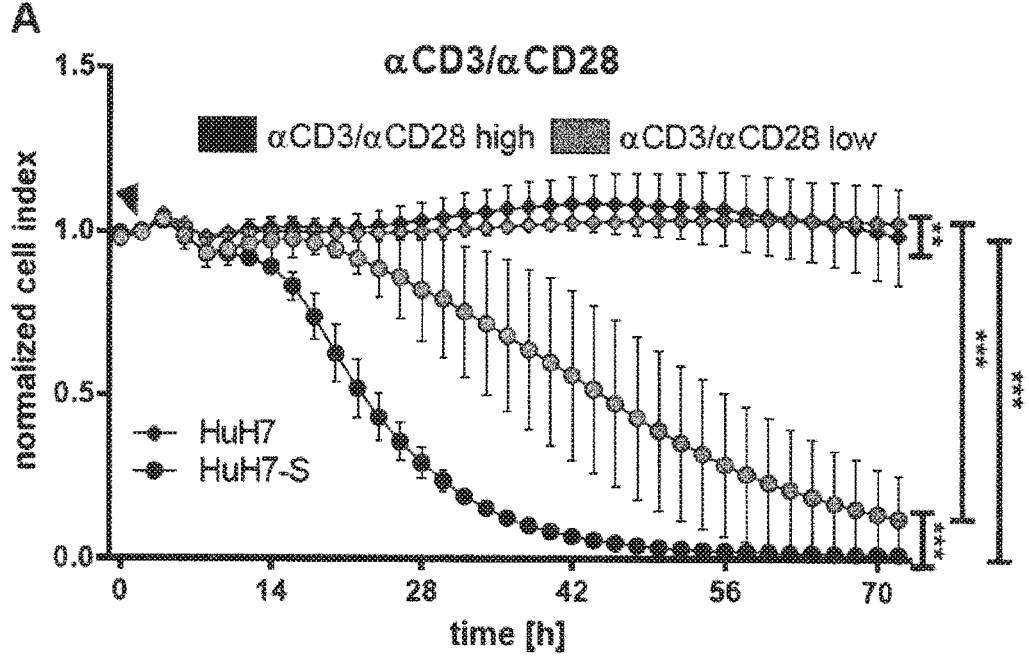
Figure 7:
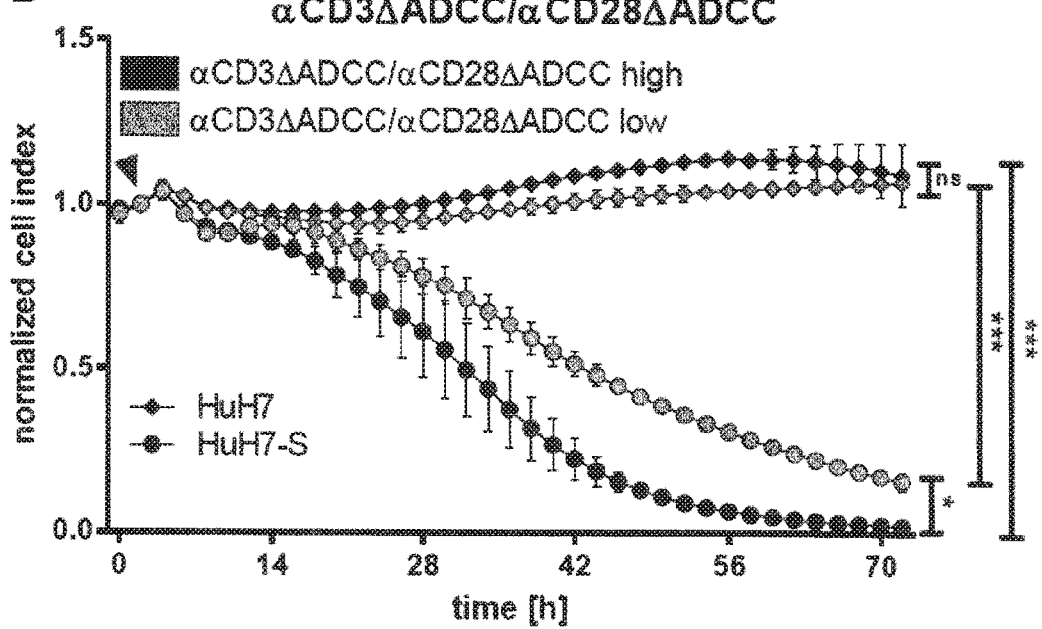

Bispecific Antibodies Provoke Elimination of Target Cells in a Concentration Dependent Manner To examine if the amount of bispecific antibodies had an effect on target cell lysis, two different amounts of bispecific constructs were used for co-culture. Therefore, the usual amount of antibodies (100 µl supernatant in total≙high) and the half of it (50 µl supernatant in total≙low) were used. The lower amount of bispecific antibodies could also induce lysis of target cells (endpoint viability of HuH7-S cells: αCD3/αCD28: 12.6%; αCD3ΔADCC/αCD28ΔADCC: 15.9%), whereas the higher amount caused elimination of target cells faster (FIG. 7) with only 1.5% (αCD3/αCD28) and 2.1% (αCD3ΔADCC/αCD28ΔADCC) of remaining viable cells. HuH7 cells were not affected in any case. Combination of either αCD3/αCD28 or αCD3ΔADCC/αCD28ΔADCC provoked killing of target cells in a concentration dependent manner.

Increased Concentrations of Effector Cells Enhance Lysis of Target Cells

Figure 8:
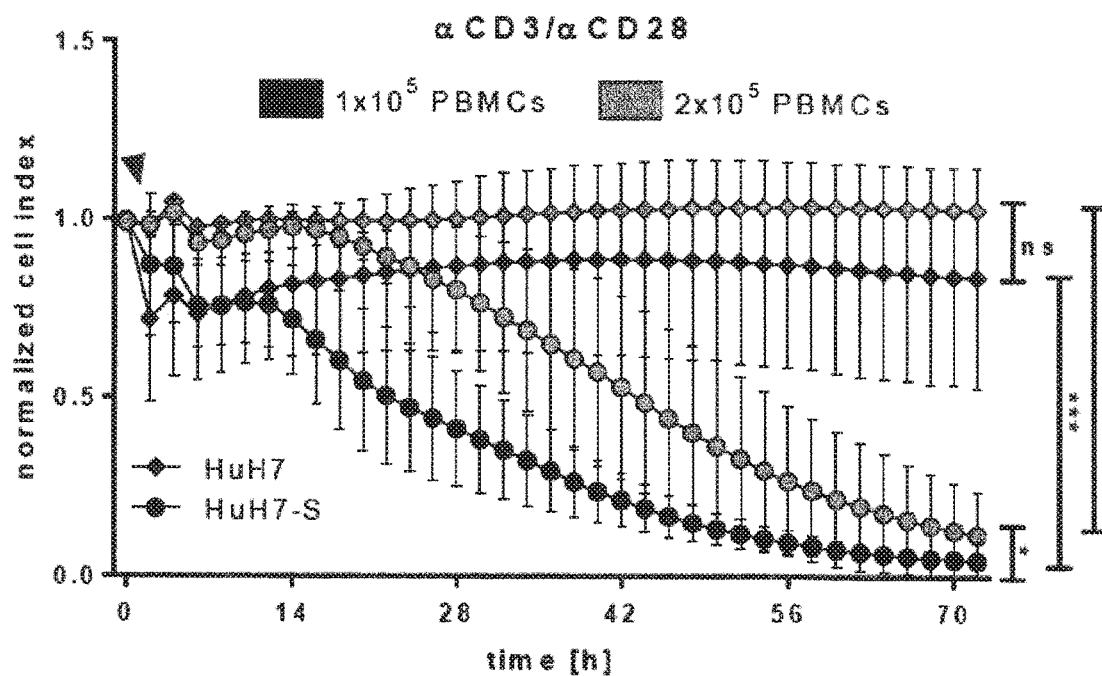

It was of further interest if the number of effector cells had an impact on the elimination of target cells. Thus, the usual amount of PBMCs used for co-culture ($1 \times 10^5$) was compared to the double amount ($2 \times 10^5$). As it is demonstrated in FIG. 8, the higher number of PBMCs induced lysis of HuH7-S cells in the presence of αCD3/αCD28 significantly faster with an endpoint viability of 4.5% compared to 11.7%, but also more HuH7 cells were killed, if the double amount of PBMCs was present (endpoint viability of HuH7 cells: $2 \times 10^5$ PBMCs: 83.8%; $1 \times 10^5$ PBMCs: 102.7%).

This data indicates that the elimination of target cells is dependent on the amount of effector cells.

Figure 9:
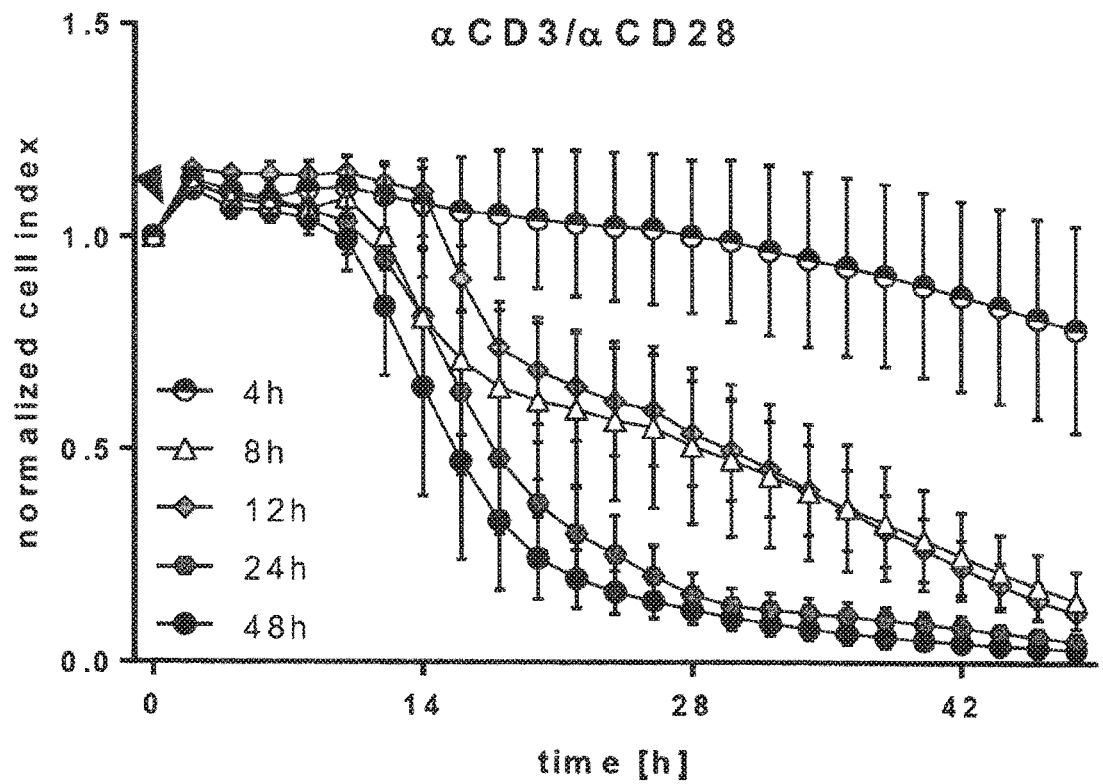
Figure 10:
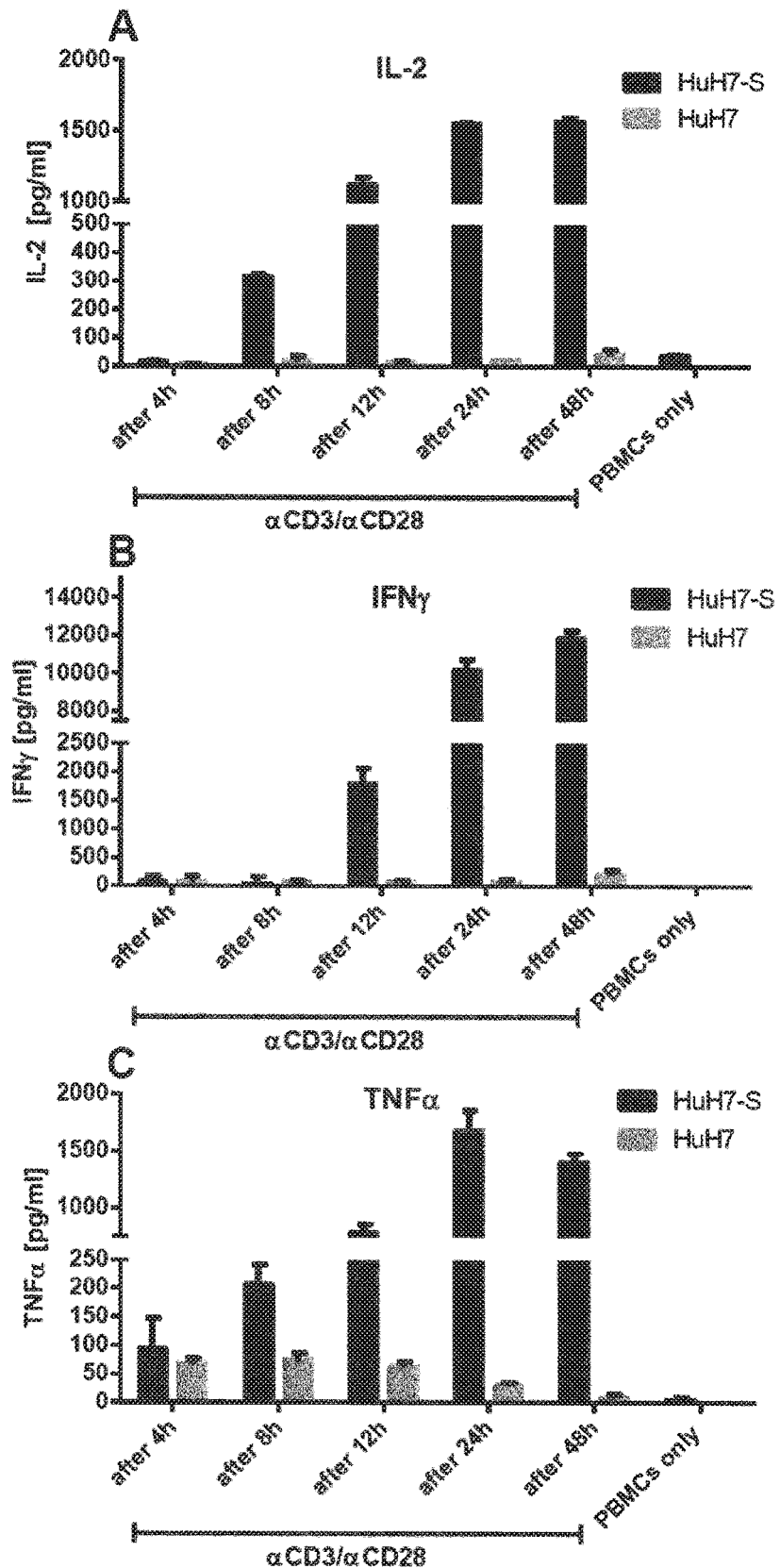

Bispecific Antibodies Mediate Killing of Target Cells After Only 8 h of Co-Culture To investigate the question, how long bispecific antibodies have to be present during co-culture to activate T cells and therefore induce cytotoxicity, the supernatant of co-cultures containing the bispecific antibodies was removed after different time periods and new DMEM standard medium was added. If supernatant containing αCD3/αCD28 was removed after 4 h, PBMCs only induced a small decrease in target cell viability (78.5%), but were not able to provoke lysis of all target cells (FIG. 9). If supernatant containing bispecific antibodies was present for 8 h or longer, PBMCs were able to cause elimination of target cells. As it is illustrated in FIG. 10, PBMCs needed more time to induce target cell lysis if stimulation with αCD3/αCD28 lasted for 8 h or 12 h compared to 24 h or 48 h, but the effect after 48 h was nearly similar (HuH7-S endpoint viability: 8 h: 14.7%; 12 h: 11.7%, 24 h: 5.1%, 48 h: 3.2%).

Bispecific Antibodies Mediate Effector Functions of T Cells During Co-Culture with Either HBsAg or Huh7-S Cells To investigate the activation and functionality of T cells during co-culture experiments, the secretion of cytokines was examined either by ELISA or FACS analysis.

Bispecific Constructs Mediate the Secretion of IFN-γ, TNF-α and IL-2

In a time line experiment it was analyzed, when PBMCs start to secret cytokines upon contact with bispecific antibodies and how dynamics develop over time. Therefore, supernatant of co-cultures was removed 4 h, 8 h, 12 h, 24 h and 48 h after addition of PBMCs and αCD3/αCD28. Cytokine production was measured by ELISAs for IL-2, IFN-γ and TNF-α. The secretion of IL-2 increased over time, but after 4 h almost no IL-2 was detectable, after 8 h the concentration was already 316 pg/ml and during the following 4 hours, the concentration almost quadrupled (1119 pg/ml). There was no further rise between 24 h and 48 h and IL-2 concentration seemed to reach a plateau at about 1550 pg/ml (FIG. 10A). IFN-γ secretion (FIG. 10B) needed more time, after 8 h still very low levels were detected. Between 8 h and 12 h, T cells started to secret IFN-γ, because its concentration accounted already for 1800 pg/ml after 12 h. Subsequently (24 h) an increase in IFN-γ production was observed, the concentration increased to around 10000 pg/ml. The highest amount was detected after 48 h (12000 pg/ml). For both, IL-2 and IFNγ, the concentration on HBsAg negative cells increased over time, with the highest amount after 48 h (IL-2: 45 pg/ml; IFNγ: 200 pg/ml) which also corresponds to observations concerning cell viability.

The secretion of TNF-α (FIG. 10C) increased up to 24 h, where it reached its peak concentration (1700 pg/ml). Then it declined and accounted for only 1400 pg/ml after 48 h. In contrast TNF-α secretion started earlier than the others, with around 100 pg/ml after 4 h followed by a steady rise up to 24 h. Interestingly, TNF-α production on HuH7 cells behaved in exactly the opposite way. With a relatively high background concentration compared to other cytokines, it showed the highest concentration after 4 h (~70 pg/ml) which declined over time and accounted for only 9 pg/ml after 48 h. PBMCs are induced to secret IL-2, IFN-γ and TN-Fα upon contact with αCD3/αCD28 during co-culture with HBsAg-expressing cells, whereas the secretion dynamics differ among the individual cytokines.

Bispecific Constructs Activate CD8+ T Cells as Well as CD4+ T Cells

Figure 11:
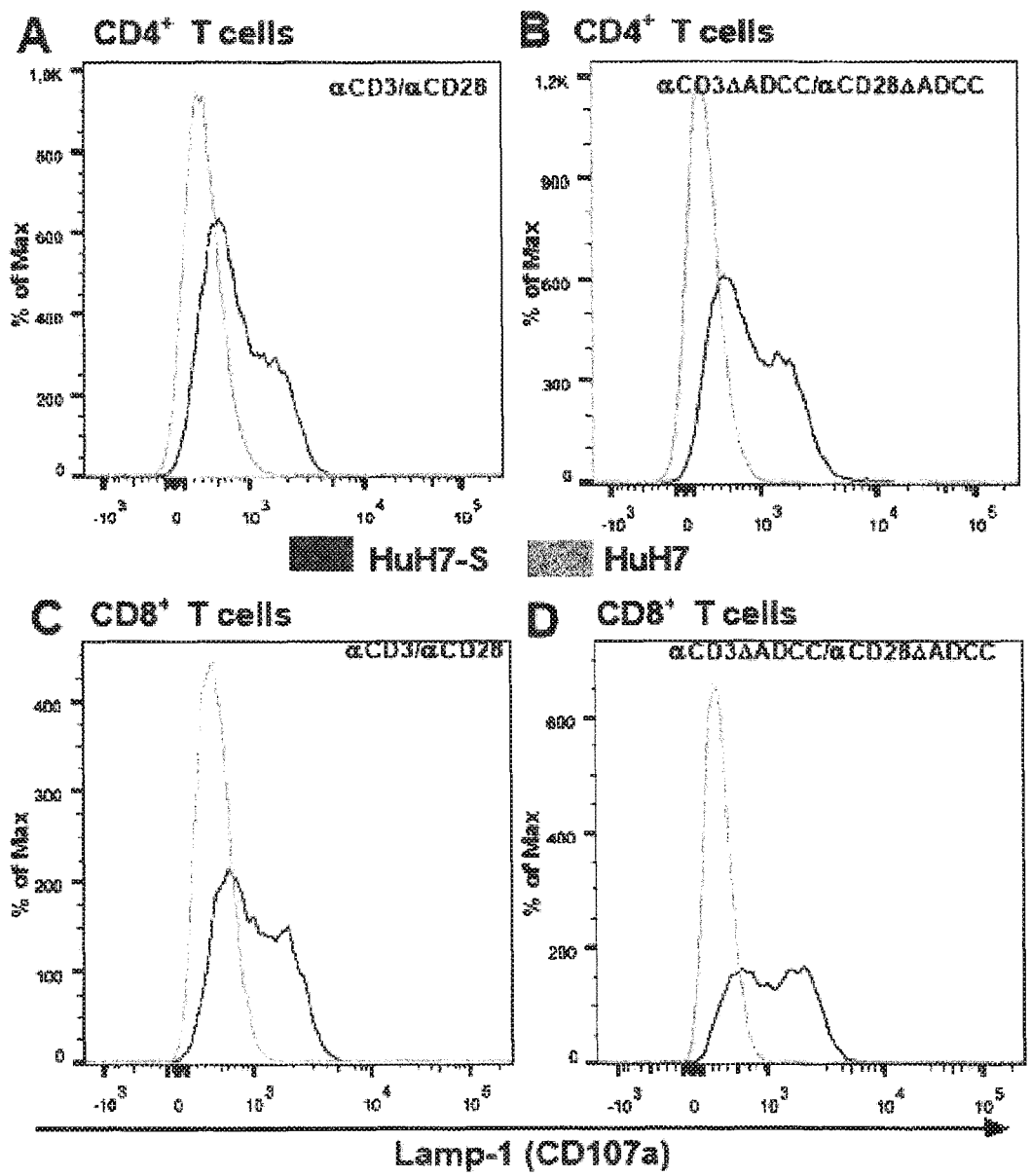

To analyze if PBMCs also show degranulation of cytotoxic vesicles, the translocation of LMAP-1 (CD107a), a degranulation marker, was investigated. After co-culture with HuH7-S/HuH7 cells in presence of αCD3/αCD28 or αCD3ΔADCC/αCD28ΔADCC, CD8+ T cells showed a clear shift in LAMP-1 staining, whereas the signal was stronger in samples stimulated with αCD3ΔADCC/αCD28ΔADCC compared to αCD3/αCD28 (FIG. 11 C, D). Interestingly, the same observation could be made for CD4+ T cells (FIG. 11 A, B). For αCD3/αCD28 the translocation of LAMP-1 was more prominent in CD8+ T cells, for αCD3ΔADCC/αCD28ΔADCC exactly the opposite.

This data demonstrates, that not only CD8+ T cells, but also CD4+ are induced to secret cytotoxic granules upon contact with the bispecific antibodies and HBsAg.

Figure 12:
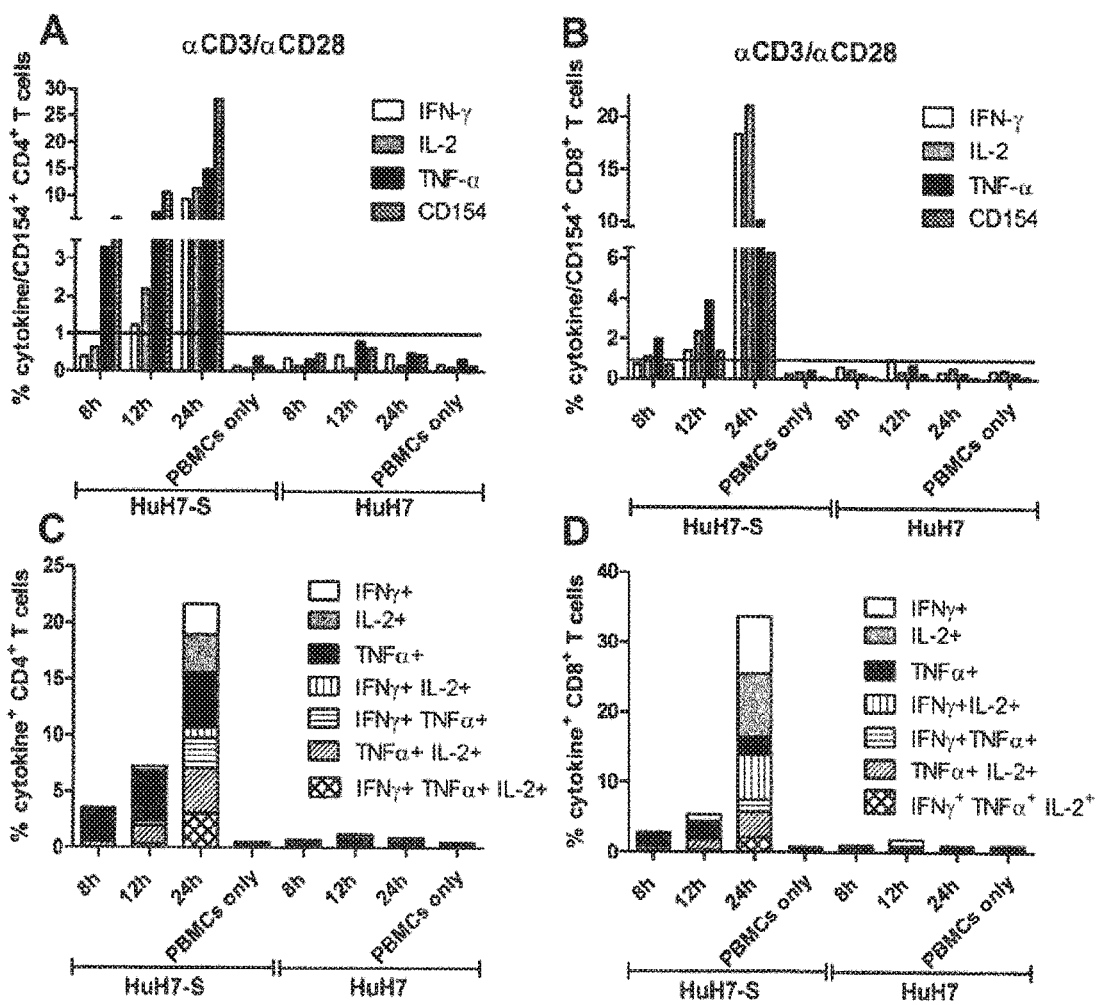

To examine polyfunctionality of T cells after co-culture experiments, PBMC were stained for IFN-γ, IL-2 and TNF-α, as well as for the activation marker CD154 (CD40L) which is predominantly expressed on CD4+ T cells, at 8 h, 12 h and 24 h after addition of PBMC and αCD3/αCD28 (FIG. 12). CD4+ T cells showed a steady increase of IFN-γ+ T cells (9.3% after 24 h), IL-2+ T cells (11.3% after 24 h), TNF-α+ T cells (14.7% after 24 h) and CD154+ T cells (28.0% after 24 h), whereas the major rise occurred between 12 h and 24 h (FIG. 12A).

The same was true for CD8+ T cells, whereas the percentage of IFN-γ+ and IL-2+ cells with 18.4% and 11.3% outnumbered CD4+ T cells. The amount of TNF-α+ and CD154+ CD8+ T cells was decreased with 10.1% and 6.25% compared to CD4+ T cells (FIG. 12B). PBMC on HuH7 cells showed no activation in any sample. Boolean combination gates were used for further analysis of T cells secreting cytokines (FIG. 12C, D). After 24 h 3.1% of CD4+ T cells and 2.1% of CD8+ T cells were IFNγ+, IL-2+ and TNFα+, indicating polyfunctionality of T cells. Therefore, αCD3/αCD28 mediates activation of PBMCs during co-culture with HuH7-S/HuH7 cells resulting in polyfunctional CD4+ and CD8+ T cells.

Figure 13:
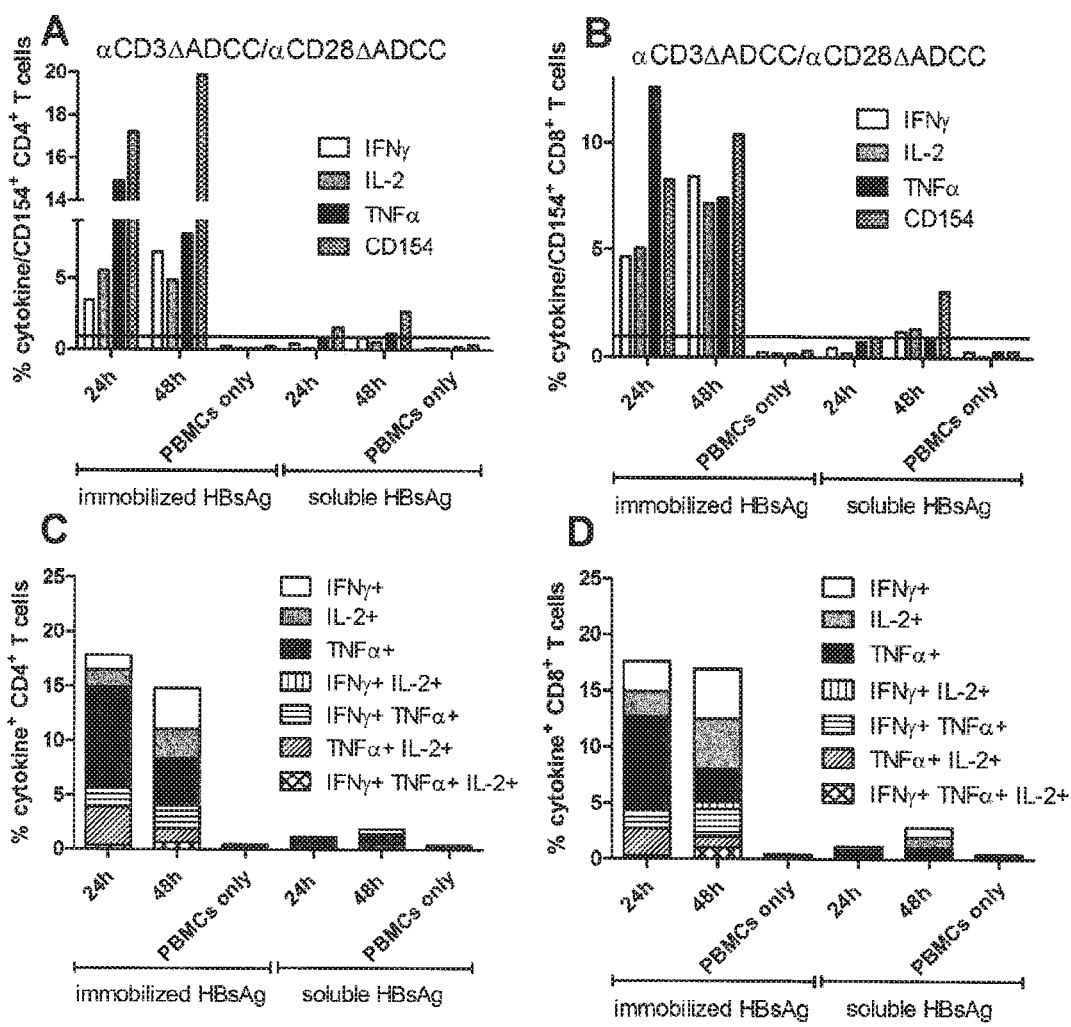

To exclude the possibility that false positive signals were detected due to unspecific binding of antibodies to dead target cells during FACS analysis, PBMC were cultured in the presence of Immobilized HBsAg. Additionally the effect of soluble HBsAg was examined, as HBV infected patients exhibit high amounts of HBsAg in their blood. PBMCs were again stained for IFN-γ, IL-2 and TNF-α, as well as for CD154, but only 24 h and 48 h after addition of PBMC and αCD3ΔADCC/αCD28ΔADCC (FIG. 13). Again CD4+ T cells showed an increase of IFN-γ+ T cells (3.4% after 24 h, 6.8% after 48 h), and CD154+ T cells (17.2% after 24 h, 19.9% after 48 h).

There were less IL-2+ T cells after 48 h (4.9%) compared to 24 h (5.5%), TNF-α+ T cells also decreased (14.9% after 24 h, 8.1% after 48 h) (FIG. 13A). CD8+ T cells only showed a decrease in TNF-α+ T cells (12.6% after 24 h, 7.4% after 48 h), whereby this reduction was also observed in ELISA (FIG. 10). The percentage of IFN-γ+, IL-2+ and CD154+ CD8+ T cells increased between 24 h and 48 h (IFNγ+: 4.7% after 24 h, 8.5% after 48 h, IL-2+: 5.1% after 24 h, 7.2% after 48 h, CD154+: 8.3% after 24 h, 10.4% after 48 h) (FIG. 13B). Again the percentage of IFN-γ+ and IL-2+ CD8+ T cells outnumbered CD4+ T cells and the amount of TNF-α+ and CD154+ CD8+ T cells was decreased compared to CD4+ T cells. After 48 h also some T cells seemed to be activated by the soluble HBsAg, as TNFα+ T cells reached 1.1% (CD4+ T cells) and 1.0% (CD8+ T cells), CD154+ T cells 2.7% (CD4+ T cells) and 3.1% (CD8+ T cells), IFNγ+ CD8+ T cells 1.2% and IL-2+ CD8+ T cells 1.4%. Again boolean gates were used for further analysis of T cells secreting cytokines (FIG. 13C, D). 0.35% (after 24 h) and 0.63% (after 48 h) of CD4+ T cells, 0.3% (after 24 h) and 1.0% (after 48 h) of CD8+ T cells were IFN-γ+, IL-2+ and TNF-α+, indicating polyfunctionality of T cells. αCD3ΔDCC/αCD28ΔADCC mediates activation of PBMCs during co-culture with immobilized HBsAg cells resulting in polyfunctional CD4+ and CD8+ T cells. The activation due to soluble HBsAg remains poor.

Figure 14:
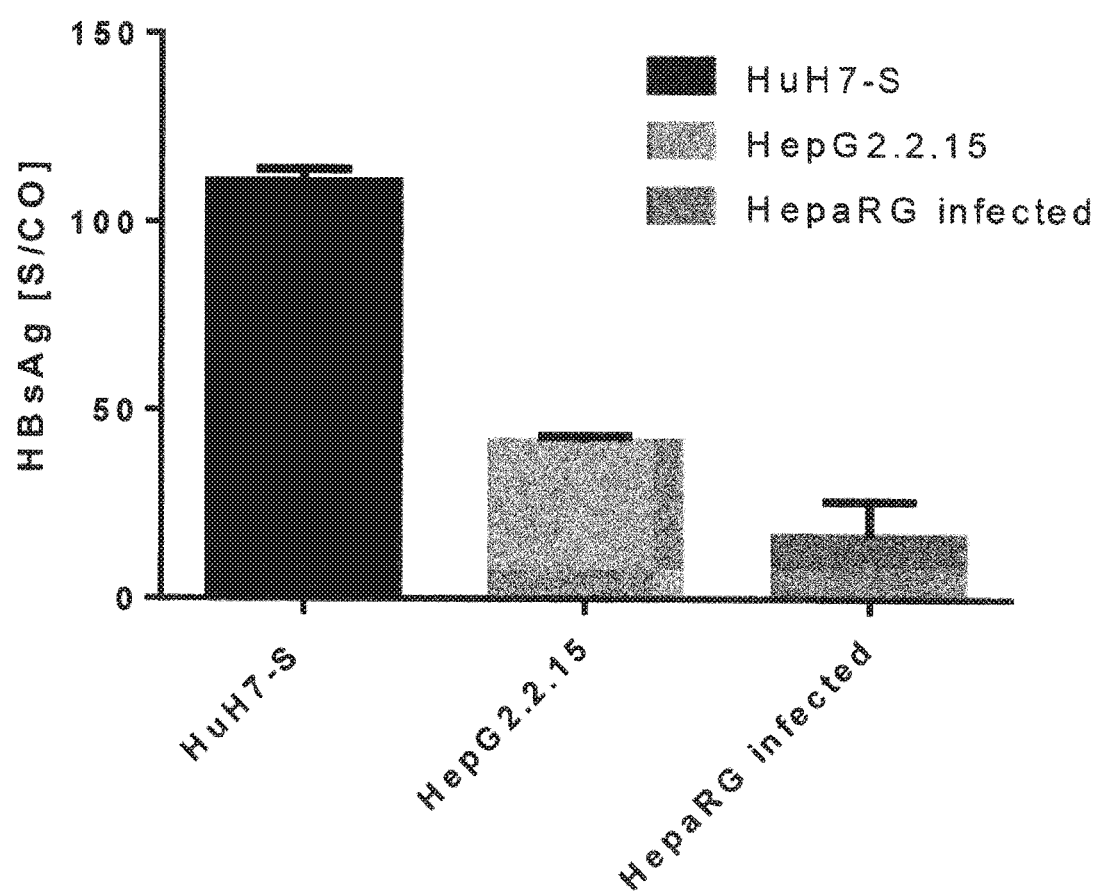

Bispecific Antibodies Mediate IFNγ Secretion and Killing of HBV Infected HepaRG Cells Finally, it was of interest, if bispecific antibodies are able to retarget T cells towards HBV infected HepaRG cells. Success of infection was tested by the measurement of HBsAg in the supernatant of infected cells. Compared to results of HuH7-S or HepG2.2.15 cells, the concentration of HBsAg produced by HBV infected HepaRG cells was very low. Additionally the values in different wells varied a lot, indicated by the relatively high standard deviation (FIG. 14).

Figure 15:
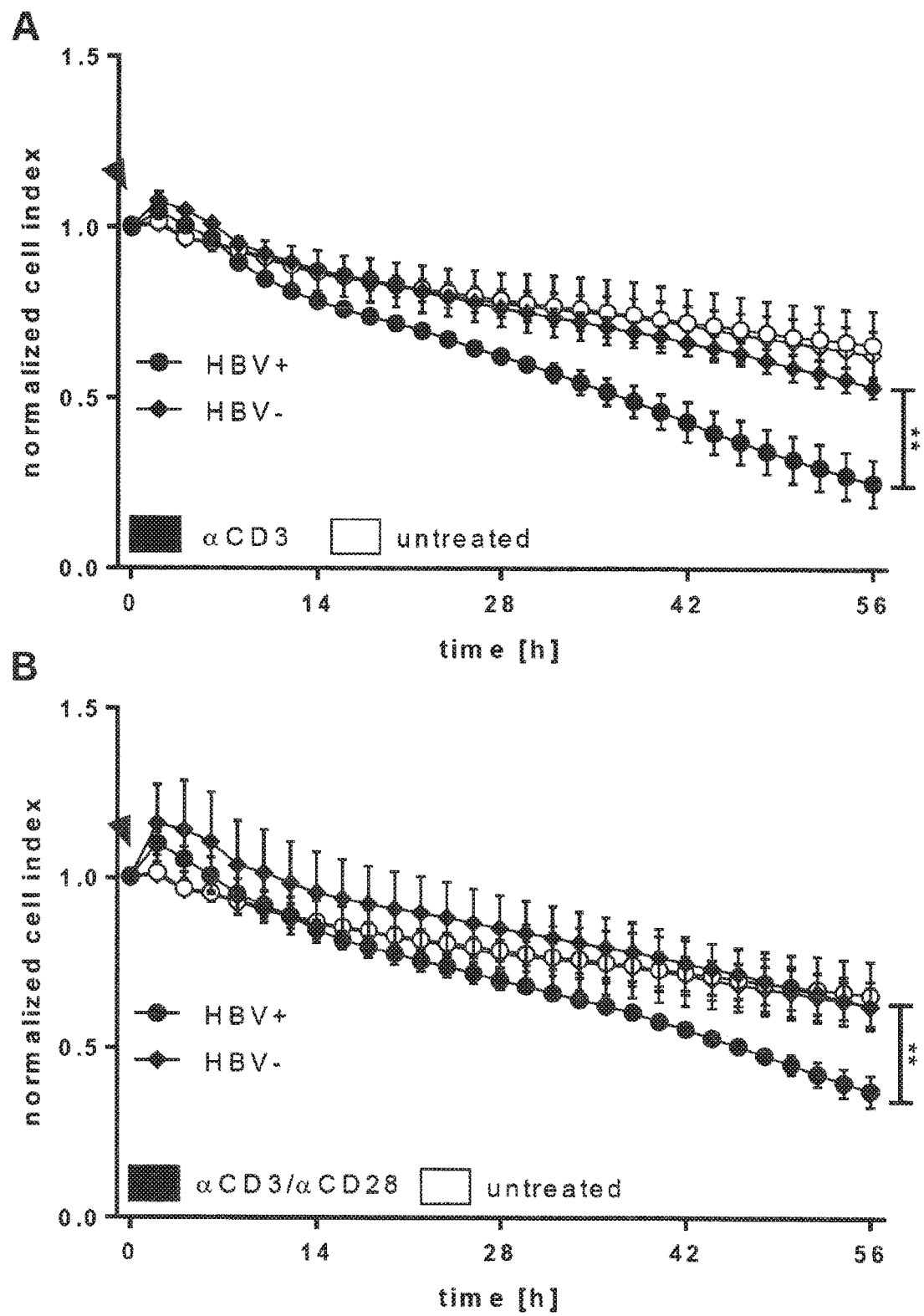

Nevertheless, the infection was successful and co-culture of PBMCs with HepaRG cells in presence of bispecific antibodies was performed. As can be seen in FIG. 15, viability of untreated cells decreased over time, with a remaining viability of 65.9% (HBV+) and 62.9% (HBV−) after 56 h. In comparison, αCD3 and the combination of αCD3/αCD28 mediated specific lysis of HBV infected HepaRG cells. αCD28 alone could not induce specific elimination of target cells. If αCD3 was present during co-culture, the viability of HBV infected cells decreased to 25.3%, while non-infected HepaRG cells remained at 53.5% (FIG. 15A). The stimulation of effector cells by αCD3/αCD28 also led to significant killing of HBV infected HepaRG cells (FIG. 15B), whereby 37.5% of target cells remained viable (not infected HepaRG cells: 62.4%).

Therefore, αCD3 or αCD3/αCD28 Induce specific lysis of HBV infected HepaRG cells.

Bispecific Antibodies Mediate Reduction of HBV-Positive Tumors in Vivo

Figure 16:
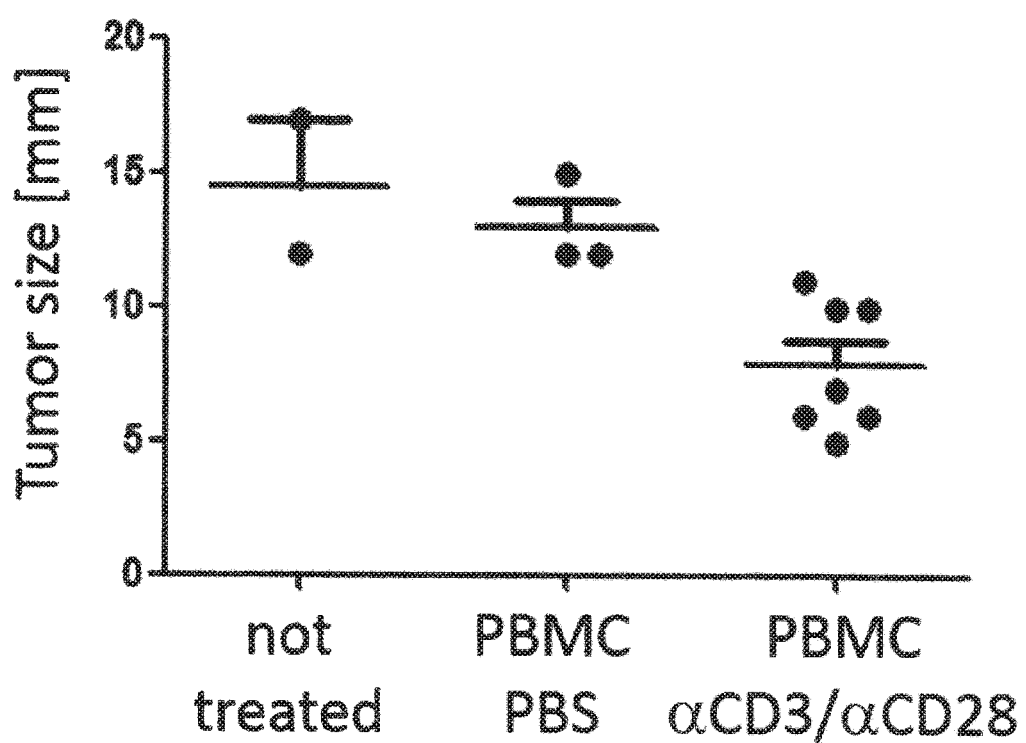

Immunodeficient mice injected with human HBV-transgenic hepatoma cell line HepG2.2.15 to develop subcutaneous HBV-positive tumors were injected with human PBMC and bispecific constructs directed against CD3 and CD28 (FIG. 16). The treatment resulted in a marked reduction in tumor size in comparison to not-treated or mock treated (animals receiving PBMC and PBS) animals. The tumor size was reduced by about fifty percent in treated animals.

The invention claimed is:

1. A polypeptide comprising:
   (a) a first set of six complementarity determining regions (CDRs) that bind to a first antigen; wherein said first set of six CDRs has the sequences of SEQ ID NOs: 1 to 6; and
   (b) a second set of six CDRs that bind to a second antigen; wherein said second set of six CDRs has the sequences of SEQ ID NOs: 25 to 30 wherein
   (i) said first antigen is Hepatitis B virus (HBV) small surface antigen; and
   (ii) said second antigen is a CD28 surface antigen, and
   wherein said CDRs are part of immunoglobulin domains.

2. The polypeptide of claim 1, wherein
   (a) said first set of six CDRs is comprised in a first scFv fragment; and/or
   (b) said second set of six CDRs is comprised in a second scFv fragment.

3. The polypeptide of claim 1, wherein said first set of six CDRs binds an epitope of said first antigen which epitope is located in said HBV small surface antigen.

4. The polypeptide of claim 1, wherein said polypeptide further comprises a dimerization region, wherein said dimerization region provides for covalent and/or non-covalent dimerization.

5. The polypeptide of claim 2, wherein said polypeptide further comprises a spacer region, said spacer region comprising a CH2 domain and a CH3 domain, said spacer region being located between
   (i) said first scFv fragment and
   (ii) said second scFv fragment in the amino acid sequence of said polypeptide,
and said CH2 domain and/or said CH3 domain being mutated in one or more positions to diminish or abolish the binding to $F_c$ receptors.

6. The polypeptide of claim 1, wherein within each set of six CDRs the order of CDRs is as follows: CDR1 of heavy chain, CDR2 of heavy chain, CDR3 of heavy chain, CDR1 of light chain, CDR2 of light chain, and CDR3 of light chain.

7. The polypeptide of claim 1, wherein said polypeptide comprises the amino acid sequence of SEQ ID NO: 44 or an amino acid sequence which exhibits at least 80% identity to SEQ ID NO: 44, provided that the CDRs of said amino acid sequence exhibiting at least 80% identity are identical to SEQ ID NOs: 1 to 6 and 25 to 30, respectively.

8. A nucleic acid molecule encoding the polypeptide of claim 1.

9. A complex comprising a first and a second polypeptide, said first polypeptide being as defined in claim 1, and the second polypeptide comprising:
   (A) a first set of six complementarity determining regions (CDRs) that bind to a first antigen; wherein said first set of six CDRs has the sequences of SEQ ID NOs: 1 to 6, 7 to 12, or 13 to 18; and
   (B) (ba) a second set of six CDRs that bind to a second antigen; wherein said second set of six CDRs has the sequences of SEQ ID NOs: 19 to 24, 25 to 30, 31 to 36, or 37 to 42, or
   (bb) a ligand capable of binding to a second antigen;
wherein
   (i) said first antigen is selected from Hepatitis B virus (HBV) small surface antigen; HBV medium surface antigen; and HBV large surface antigen; and
   (ii) said second antigen is selected from surface antigens presented by immune effector cells, and
wherein said CDRs are part of immunoglobulin domains;
wherein
   (a) there is at least one covalent linkage between said first and said second polypeptide; or
   (b) said first and said second polypeptide are bound to each other non-covalently.

10. A composition comprising
    (A) a first polypeptide according to claim 1 and a second polypeptide comprising:
       (a) a first set of six complementarity determining regions (CDRs) that bind to a first antigen; wherein said first set of six CDRs has the sequences of SEQ ID NOs: 1 to 6, 7 to 12, or 13 to 18; and
       (b) (ba) a second set of six CDRs that bind to a second antigen; wherein said second set of six CDRs has the sequences of SEQ ID NOs: 19 to 24, 25 to 30, 31 to 36, or 37 to 42, or
       (bb) a ligand capable of binding to a second antigen;
    wherein
       (i) said first antigen is selected from Hepatitis B virus (HBV) small surface antigen; HBV medium surface antigen; and HBV large surface antigen; and
       (ii) said second antigen is selected from surface antigens presented by immune effector cells, and
    wherein said CDRs are part of immunoglobulin domains and/or
    (B) one or more complexes according to claim 9,
    wherein the first polypeptide and the second polypeptide are distinct from each other with regard to the first antigen and/or the second antigen to which they bind.

11. The complex of claim 9 or the composition of claim 10, wherein said complex and said composition comprise or consist of a tetravalent antibody which is bispecific, trispecific or tetraspecific.

12. A pharmaceutical composition comprising one or more polypeptides of claim 1, one or more complexes of claim 9 and/or one or more compositions of claim 10.

13. An in vitro or ex vivo immune effector cell comprising a polypeptide of claim 1 or a complex according to claim 9 bound to a surface antigen of said immune effector cell.

* * * * *

```
                         SEQUENCE LISTING

<160> NUMBER OF SEQ ID NOS: 49

<210> SEQ ID NO 1
    <211> LENGTH: 8
    <212> TYPE: PRT
    <213> ORGANISM: Artificial Sequence
    <220> FEATURE:
    <223> OTHER INFORMATION: CDR1 of scFv C8 heavy chain

<400> SEQUENCE: 1

Gly Phe Thr Phe Ser Gly Tyr Ala
    1               5

<210> SEQ ID NO 2
    <211> LENGTH: 8
    <212> TYPE: PRT
    <213> ORGANISM: Artificial Sequence
    <220> FEATURE:
    <223> OTHER INFORMATION: CDR2 of scFv C8 heavy chain

<400> SEQUENCE: 2

Ile Ser Gly Ser Gly Gly Ser Thr
    1               5

<210> SEQ ID NO 3
    <211> LENGTH: 21
    <212> TYPE: PRT
    <213> ORGANISM: Artificial Sequence
    <220> FEATURE:
    <223> OTHER INFORMATION: CDR3 of scFv C8 heavy chain

<400> SEQUENCE: 3

Ala Lys Pro Pro Gly Arg Gln Glu Tyr Tyr Gly Ser Ser Ile Tyr Tyr
    1               5                   10                  15

Phe Pro Leu Gly Asn
                20

<210> SEQ ID NO 4
```

```
<211> LENGTH: 6
<212> TYPE: PRT
<213> ORGANISM: Artificial Sequence
<220> FEATURE:
<223> OTHER INFORMATION: CDR1 of scFv C8 light chain

<400> SEQUENCE: 4

Asn Ile Gly Ser Lys Ser
1               5

<210> SEQ ID NO 5
<211> LENGTH: 3
<212> TYPE: PRT
<213> ORGANISM: Artificial Sequence
<220> FEATURE:
<223> OTHER INFORMATION: CDR2 of scFv C8 light chain

<400> SEQUENCE: 5

Asp Asp Ser
1

<210> SEQ ID NO 6
<211> LENGTH: 11
<212> TYPE: PRT
<213> ORGANISM: Artificial Sequence
<220> FEATURE:
<223> OTHER INFORMATION: CDR3 of scFv C8 light chain

<400> SEQUENCE: 6

Gln Val Trp Asp Ser Ser Ser Asp Leu Val Val
1               5                   10

<210> SEQ ID NO 7
<211> LENGTH: 8
<212> TYPE: PRT
<213> ORGANISM: Artificial Sequence
<220> FEATURE:
<223> OTHER INFORMATION: CDR1 of scFv 5F9 heavy chain

<400> SEQUENCE: 7

Gly Phe Thr Phe Asn Asn Tyr Ala
1               5

<210> SEQ ID NO 8
<211> LENGTH: 8
<212> TYPE: PRT
<213> ORGANISM: Artificial Sequence
<220> FEATURE:
<223> OTHER INFORMATION: CDR2 of scFv 5F9 heavy chain

<400> SEQUENCE: 8

Ile Asn Ser Asp Gly Arg Ser Thr
1               5

<210> SEQ ID NO 9
<211> LENGTH: 8
<212> TYPE: PRT
<213> ORGANISM: Artificial Sequence
<220> FEATURE:
<223> OTHER INFORMATION: CDR3 of scFv 5F9 heavy chain

<400> SEQUENCE: 9

Ala Arg Thr Phe Tyr Ala Asp Tyr
1               5

<210> SEQ ID NO 10
<211> LENGTH: 6
```

```
<212> TYPE: PRT
<213> ORGANISM: Artificial Sequence
<220> FEATURE:
<223> OTHER INFORMATION: CDR1 of scFv 5F9 light chain

<400> SEQUENCE: 10

Gln Asn Val Asp Thr Thr
1               5

<210> SEQ ID NO 11
<211> LENGTH: 3
<212> TYPE: PRT
<213> ORGANISM: Artificial Sequence
<220> FEATURE:
<223> OTHER INFORMATION: CDR2 of scFv 5F9 light chain

<400> SEQUENCE: 11

Trp Ala Ser
1

<210> SEQ ID NO 12
<211> LENGTH: 9
<212> TYPE: PRT
<213> ORGANISM: Artificial Sequence
<220> FEATURE:
<223> OTHER INFORMATION: CDR3 of scFv 5F9 light chain

<400> SEQUENCE: 12

Gln Gln Tyr Ser Ile Phe Pro Tyr Thr
1               5

<210> SEQ ID NO 13
<211> LENGTH: 8
<212> TYPE: PRT
<213> ORGANISM: Artificial Sequence
<220> FEATURE:
<223> OTHER INFORMATION: CDR1 of scFv 5A19 heavy chain

<400> SEQUENCE: 13

Gly Phe Thr Phe Ser Ser Tyr Ala
1               5

<210> SEQ ID NO 14
<211> LENGTH: 8
<212> TYPE: PRT
<213> ORGANISM: Artificial Sequence
<220> FEATURE:
<223> OTHER INFORMATION: CDR2 of scFv 5A19 heavy chain

<400> SEQUENCE: 14

Val Ser Ser Asp Gly Ser Tyr Ala
1               5

<210> SEQ ID NO 15
<211> LENGTH: 9
<212> TYPE: PRT
<213> ORGANISM: Artificial Sequence
<220> FEATURE:
<223> OTHER INFORMATION: CDR3 of scFv 5A19 heavy chain

<400> SEQUENCE: 15

Ala Ser Phe Asn Trp Asp Val Ala Tyr
1               5

<210> SEQ ID NO 16
<211> LENGTH: 12
<212> TYPE: PRT
```

```
<213> ORGANISM: Artificial Sequence
<220> FEATURE:
<223> OTHER INFORMATION: CDR1 of scFv 5A19 light chain

<400> SEQUENCE: 16

Gln Ser Leu Leu Asn Thr Arg Thr Arg Lys Ser Tyr
1               5                   10

<210> SEQ ID NO 17
<211> LENGTH: 3
<212> TYPE: PRT
<213> ORGANISM: Artificial Sequence
<220> FEATURE:
<223> OTHER INFORMATION: CDR2 of scFv 5A19 light chain

<400> SEQUENCE: 17

Trp Ala Ser
1

<210> SEQ ID NO 18
<211> LENGTH: 8
<212> TYPE: PRT
<213> ORGANISM: Artificial Sequence
<220> FEATURE:
<223> OTHER INFORMATION: CDR3 of scFv 5A19 light chain

<400> SEQUENCE: 18

Lys Gln Ser Tyr Ser Leu Tyr Thr
1               5

<210> SEQ ID NO 19
<211> LENGTH: 8
<212> TYPE: PRT
<213> ORGANISM: Artificial Sequence
<220> FEATURE:
<223> OTHER INFORMATION: CDR1 of scFv OKT3 heavy chain

<400> SEQUENCE: 19

Gly Tyr Thr Phe Thr Arg Tyr Thr
1               5

<210> SEQ ID NO 20
<211> LENGTH: 8
<212> TYPE: PRT
<213> ORGANISM: Artificial Sequence
<220> FEATURE:
<223> OTHER INFORMATION: CDR2 of scFv OKT3 heavy chain

<400> SEQUENCE: 20

Ile Asn Pro Ser Arg Gly Tyr Thr
1               5

<210> SEQ ID NO 21
<211> LENGTH: 12
<212> TYPE: PRT
<213> ORGANISM: Artificial Sequence
<220> FEATURE:
<223> OTHER INFORMATION: CDR3 of scFv OKT3 heavy chain

<400> SEQUENCE: 21

Ala Arg Tyr Tyr Asp Asp His Tyr Cys Leu Asp Tyr
1               5                   10

<210> SEQ ID NO 22
<211> LENGTH: 5
<212> TYPE: PRT
<213> ORGANISM: Artificial Sequence
```

```
<220> FEATURE:
<223> OTHER INFORMATION: CDR1 of scFv OKT3 light chain

<400> SEQUENCE: 22

Ser Ser Val Ser Tyr
1               5

<210> SEQ ID NO 23
<211> LENGTH: 3
<212> TYPE: PRT
<213> ORGANISM: Artificial Sequence
<220> FEATURE:
<223> OTHER INFORMATION: CDR2 of scFv OKT3 light chain

<400> SEQUENCE: 23

Asp Thr Ser
1

<210> SEQ ID NO 24
<211> LENGTH: 9
<212> TYPE: PRT
<213> ORGANISM: Artificial Sequence
<220> FEATURE:
<223> OTHER INFORMATION: CDR3 of scFv OKT3 light chain

<400> SEQUENCE: 24

Gln Gln Trp Ser Ser Asn Pro Phe Thr
1               5

<210> SEQ ID NO 25
<211> LENGTH: 8
<212> TYPE: PRT
<213> ORGANISM: Artificial Sequence
<220> FEATURE:
<223> OTHER INFORMATION: CDR1 of scFv 9.3 heavy chain

<400> SEQUENCE: 25

Gly Phe Ser Leu Ser Asp Tyr Gly
1               5

<210> SEQ ID NO 26
<211> LENGTH: 7
<212> TYPE: PRT
<213> ORGANISM: Artificial Sequence
<220> FEATURE:
<223> OTHER INFORMATION: CDR2 of scFv 9.3 heavy chain

<400> SEQUENCE: 26

Ile Trp Ala Gly Gly Gly Thr
1               5

<210> SEQ ID NO 27
<211> LENGTH: 14
<212> TYPE: PRT
<213> ORGANISM: Artificial Sequence
<220> FEATURE:
<223> OTHER INFORMATION: CDR3 of scFv 9.3 heavy chain

<400> SEQUENCE: 27

Ala Arg Asp Lys Gly Tyr Ser Tyr Tyr Tyr Ser Met Asp Tyr
1               5                   10

<210> SEQ ID NO 28
<211> LENGTH: 10
<212> TYPE: PRT
<213> ORGANISM: Artificial Sequence
<220> FEATURE:
```

<223> OTHER INFORMATION: CDR1 of scFv 9.3 light chain

<400> SEQUENCE: 28

Glu Ser Val Glu Tyr Tyr Val Thr Ser Leu
1               5                   10

<210> SEQ ID NO 29
<211> LENGTH: 3
<212> TYPE: PRT
<213> ORGANISM: Artificial Sequence
<220> FEATURE:
<223> OTHER INFORMATION: CDR2 of scFv 9.3 light chain

<400> SEQUENCE: 29

Ala Ala Ser
1

<210> SEQ ID NO 30
<211> LENGTH: 9
<212> TYPE: PRT
<213> ORGANISM: Artificial Sequence
<220> FEATURE:
<223> OTHER INFORMATION: CDR3 of scFv 9.3 light chain

<400> SEQUENCE: 30

Gln Gln Ser Arg Lys Val Pro Tyr Thr
1               5

<210> SEQ ID NO 31
<211> LENGTH: 8
<212> TYPE: PRT
<213> ORGANISM: Artificial Sequence
<220> FEATURE:
<223> OTHER INFORMATION: CDR1 of scFv A9 heavy chain

<400> SEQUENCE: 31

Gly Tyr Thr Phe Thr Asn Tyr Trp
1               5

<210> SEQ ID NO 32
<211> LENGTH: 8
<212> TYPE: PRT
<213> ORGANISM: Artificial Sequence
<220> FEATURE:
<223> OTHER INFORMATION: CDR2 of scFv A9 heavy chain

<400> SEQUENCE: 32

Ile Tyr Pro Gly Gly Gly Tyr Thr
1               5

<210> SEQ ID NO 33
<211> LENGTH: 10
<212> TYPE: PRT
<213> ORGANISM: Artificial Sequence
<220> FEATURE:
<223> OTHER INFORMATION: CDR3 of scFv A9 heavy chain

<400> SEQUENCE: 33

Ala Arg Ser Ala Ser Trp Tyr Phe Asp Val
1               5                   10

<210> SEQ ID NO 34
<211> LENGTH: 9
<212> TYPE: PRT
<213> ORGANISM: Artificial Sequence
<220> FEATURE:
<223> OTHER INFORMATION: CDR1 of scFv A9 light chain

```
<400> SEQUENCE: 34

Thr Gly Thr Val Thr Thr Ser Asn Tyr
1               5

<210> SEQ ID NO 35
<211> LENGTH: 3
<212> TYPE: PRT
<213> ORGANISM: Artificial Sequence
<220> FEATURE:
<223> OTHER INFORMATION: CDR2 of scFv A9 light chain

<400> SEQUENCE: 35

His Thr Asn
1

<210> SEQ ID NO 36
<211> LENGTH: 9
<212> TYPE: PRT
<213> ORGANISM: Artificial Sequence
<220> FEATURE:
<223> OTHER INFORMATION: CDR3 of scFv A9 light chain

<400> SEQUENCE: 36

Ala Leu Trp Tyr Asn Asn His Trp Val
1               5

<210> SEQ ID NO 37
<211> LENGTH: 8
<212> TYPE: PRT
<213> ORGANISM: Artificial Sequence
<220> FEATURE:
<223> OTHER INFORMATION: CDR1 of scFv NCAM29.2 heavy chain

<400> SEQUENCE: 37

Gly Phe Thr Phe Ser Ser Phe Gly
1               5

<210> SEQ ID NO 38
<211> LENGTH: 8
<212> TYPE: PRT
<213> ORGANISM: Artificial Sequence
<220> FEATURE:
<223> OTHER INFORMATION: CDR2 of scFv NCAM29.2 heavy chain

<400> SEQUENCE: 38

Ile Ser Ser Gly Ser Tyr Ala Ile
1               5

<210> SEQ ID NO 39
<211> LENGTH: 14
<212> TYPE: PRT
<213> ORGANISM: Artificial Sequence
<220> FEATURE:
<223> OTHER INFORMATION: CDR3 of scFv NCAM29.2 heavy chain

<400> SEQUENCE: 39

Val Arg Gly Arg Arg Leu Gly Glu Gly Tyr Ala Met Asp Tyr
1               5                   10

<210> SEQ ID NO 40
<211> LENGTH: 12
<212> TYPE: PRT
<213> ORGANISM: Artificial Sequence
<220> FEATURE:
<223> OTHER INFORMATION: CDR1 of scFv NCAM29.2 light chain
```

-continued

<400> SEQUENCE: 40

Gln Ser Leu Leu Tyr Ser Ser Asn Gln Lys Asn Tyr
1               5                   10

<210> SEQ ID NO 41
<211> LENGTH: 3
<212> TYPE: PRT
<213> ORGANISM: Artificial Sequence
<220> FEATURE:
<223> OTHER INFORMATION: CDR2 of scFv NCAM29.2 light chain

<400> SEQUENCE: 41

Trp Ala Ser
1

<210> SEQ ID NO 42
<211> LENGTH: 7
<212> TYPE: PRT
<213> ORGANISM: Artificial Sequence
<220> FEATURE:
<223> OTHER INFORMATION: CDR3 of scFv NCAM29.2 light chain

<400> SEQUENCE: 42

Gln Gln Tyr Ser Ser Trp Thr
1               5

<210> SEQ ID NO 43
<211> LENGTH: 794
<212> TYPE: PRT
<213> ORGANISM: Artificial Sequence
<220> FEATURE:
<223> OTHER INFORMATION: Anti-HBsAg scFv [C8]^Glycin-Serin-Linker^hIgG1-
    Fc[C245S,L259F,L260E,G262A,A355T]^StrepTag^Glycin-Linker^anti-CD3
    scFv [OKT3]

<400> SEQUENCE: 43

Met Asp Phe Glu Val Gln Ile Phe Ser Phe Leu Leu Ile Ser Ala Ser
1               5                   10                  15

Val Ile Met Ser Arg Met Ala Glu Val Gln Leu Val Glu Ser Gly Gly
            20                  25                  30

Gly Leu Leu Gln Pro Gly Gly Ser Leu Arg Leu Ser Cys Ala Ala Ser
        35                  40                  45

Gly Phe Thr Phe Ser Gly Tyr Ala Met Ser Trp Val Arg Gln Ala Pro
    50                  55                  60

Gly Lys Gly Leu Glu Trp Val Ser Ser Ile Ser Gly Ser Gly Gly Ser
65                  70                  75                  80

Thr Tyr Tyr Ala Asp Ser Val Lys Gly Arg Phe Thr Ile Ser Arg Asp
                85                  90                  95

Asn Ser Lys Asn Thr Leu Tyr Leu Gln Met Asn Ser Leu Arg Ala Glu
            100                 105                 110

Asp Thr Ala Leu Tyr Tyr Cys Ala Lys Pro Pro Gly Arg Gln Glu Tyr
        115                 120                 125

Tyr Gly Ser Ser Ile Tyr Tyr Phe Pro Leu Gly Asn Trp Gly Gln Gly
    130                 135                 140

Thr Leu Val Thr Val Ser Ser Ala Ser Thr Lys Gly Pro Lys Leu Glu
145                 150                 155                 160

Glu Gly Glu Phe Ser Glu Ala Arg Val Gln Ser Ala Leu Thr Gln Pro
                165                 170                 175

Ala Ser Val Ser Val Ala Pro Gly Gln Thr Ala Arg Ile Thr Cys Gly
            180                 185                 190

-continued

Gly Asn Asn Ile Gly Ser Lys Ser Val His Trp Tyr Gln Gln Lys Pro
            195                 200                 205

Gly Gln Ala Pro Val Leu Val Val Tyr Asp Asp Ser Asp Arg Pro Ser
        210                 215                 220

Gly Ile Pro Glu Arg Phe Ser Gly Ser Asn Ser Gly Asn Thr Ala Thr
225                 230                 235                 240

Leu Thr Ile Ser Arg Val Glu Ala Gly Asp Glu Ala Asp Tyr Tyr Cys
                245                 250                 255

Gln Val Trp Asp Ser Ser Ser Asp Leu Val Val Phe Gly Gly Gly Thr
            260                 265                 270

Lys Leu Thr Val Leu Gly Asn Ser Gly Gly Gly Ser Gly Gly Gly
        275                 280                 285

Gly Ser Gly Gly Gly Ser Ala Ser Glu Pro Lys Ser Ser Asp Lys
        290                 295                 300

Thr His Thr Cys Pro Pro Cys Pro Ala Pro Glu Phe Glu Gly Ala Pro
305                 310                 315                 320

Ser Val Phe Leu Phe Pro Pro Lys Pro Lys Asp Thr Leu Met Ile Ser
                325                 330                 335

Arg Thr Pro Glu Val Thr Cys Val Val Val Asp Val Ser His Glu Asp
            340                 345                 350

Pro Glu Val Lys Phe Asn Trp Tyr Val Asp Gly Val Glu Val His Asn
        355                 360                 365

Ala Lys Thr Lys Pro Arg Glu Glu Gln Tyr Asn Ser Thr Tyr Arg Val
        370                 375                 380

Val Ser Val Leu Thr Val Leu His Gln Asp Trp Leu Asn Gly Lys Glu
385                 390                 395                 400

Tyr Lys Cys Lys Val Ser Asn Lys Ala Leu Pro Thr Pro Ile Glu Lys
                405                 410                 415

Thr Ile Ser Lys Ala Lys Gly Gln Pro Arg Glu Pro Gln Val Tyr Thr
            420                 425                 430

Leu Pro Pro Ser Arg Asp Glu Leu Thr Lys Asn Gln Val Ser Leu Thr
        435                 440                 445

Cys Leu Val Lys Gly Phe Tyr Pro Ser Asp Ile Ala Val Glu Trp Glu
450                 455                 460

Ser Asn Gly Gln Pro Glu Asn Asn Tyr Lys Thr Thr Pro Pro Val Leu
465                 470                 475                 480

Asp Ser Asp Gly Ser Phe Phe Leu Tyr Ser Lys Leu Thr Val Asp Lys
                485                 490                 495

Ser Arg Trp Gln Gln Gly Asn Val Phe Ser Cys Ser Val Met His Glu
            500                 505                 510

Ala Leu His Asn His Tyr Thr Gln Lys Ser Leu Ser Leu Ser Pro Gly
        515                 520                 525

Lys Asp Pro Gly Trp Ser His Pro Gln Phe Glu Lys Ser Arg Gly Gly
        530                 535                 540

Gly Gly Gln Val Gln Leu Gln Gln Ser Gly Ala Glu Leu Ala Arg Pro
545                 550                 555                 560

Gly Ala Ser Val Lys Met Ser Cys Lys Ala Ser Gly Tyr Thr Phe Thr
                565                 570                 575

Arg Tyr Thr Met His Trp Val Lys Gln Arg Pro Gly Gln Gly Leu Glu
            580                 585                 590

Trp Ile Gly Tyr Ile Asn Pro Ser Arg Gly Tyr Thr Asn Tyr Asn Gln
        595                 600                 605

Lys Phe Lys Asp Lys Ala Thr Leu Thr Thr Asp Lys Ser Ser Ser Thr

```
            610                 615                 620
Ala Tyr Met Gln Leu Ser Ser Leu Thr Ser Glu Asp Ser Ala Val Tyr
625                 630                 635                 640

Tyr Cys Ala Arg Tyr Tyr Asp Asp His Tyr Cys Leu Asp Tyr Trp Gly
            645                 650                 655

Gln Gly Thr Thr Leu Thr Val Ser Ser Gly Asn Ser Gly Gly Gly
            660                 665                 670

Ser Gly Gly Gly Ser Gly Gly Gly Ser Ala Ser Gln Ile Val
        675                 680                 685

Leu Thr Gln Ser Pro Ala Ile Met Ser Ala Ser Pro Gly Glu Lys Val
690                 695                 700

Thr Met Thr Cys Ser Ala Ser Ser Ser Val Ser Tyr Met Asn Trp Tyr
705                 710                 715                 720

Gln Gln Lys Ser Gly Thr Ser Pro Lys Arg Trp Ile Tyr Asp Thr Ser
            725                 730                 735

Lys Leu Ala Ser Gly Val Pro Ala His Phe Arg Gly Ser Gly Ser Gly
            740                 745                 750

Thr Ser Tyr Ser Leu Thr Ile Ser Gly Met Glu Ala Glu Asp Ala Ala
        755                 760                 765

Thr Tyr Tyr Cys Gln Gln Trp Ser Ser Asn Pro Phe Thr Phe Gly Ser
770                 775                 780

Gly Thr Lys Leu Glu Ile Asn Gly Asn Ser
785                 790

<210> SEQ ID NO 44
<211> LENGTH: 793
<212> TYPE: PRT
<213> ORGANISM: Artificial Sequence
<220> FEATURE:
<223> OTHER INFORMATION: Anti-HBsAg scFv [C8]^Glycin-Serin-Linker^hIgG1-
      Fc[C245S,L259F,L26 0E,G262A,A355T]^StrepTag^Glycin-Linker^ anti-
      CD28 scFv [9.3]

<400> SEQUENCE: 44

Met Asp Phe Glu Val Gln Ile Phe Ser Phe Leu Leu Ile Ser Ala Ser
1               5                   10                  15

Val Ile Met Ser Arg Met Ala Glu Val Gln Leu Val Glu Ser Gly Gly
            20                  25                  30

Gly Leu Leu Gln Pro Gly Gly Ser Leu Arg Leu Ser Cys Ala Ala Ser
        35                  40                  45

Gly Phe Thr Phe Ser Gly Tyr Ala Met Ser Trp Val Arg Gln Ala Pro
50                  55                  60

Gly Lys Gly Leu Glu Trp Val Ser Ser Ile Ser Gly Ser Gly Gly Ser
65                  70                  75                  80

Thr Tyr Tyr Ala Asp Ser Val Lys Gly Arg Phe Thr Ile Ser Arg Asp
            85                  90                  95

Asn Ser Lys Asn Thr Leu Tyr Leu Gln Met Asn Ser Leu Arg Ala Glu
            100                 105                 110

Asp Thr Ala Leu Tyr Tyr Cys Ala Lys Pro Pro Gly Arg Gln Glu Tyr
        115                 120                 125

Tyr Gly Ser Ser Ile Tyr Tyr Phe Pro Leu Gly Asn Trp Gly Gln Gly
        130                 135                 140

Thr Leu Val Thr Val Ser Ser Ala Ser Thr Lys Gly Pro Lys Leu Glu
145                 150                 155                 160

Glu Gly Glu Phe Ser Glu Ala Arg Val Gln Ser Ala Leu Thr Gln Pro
            165                 170                 175
```

-continued

```
Ala Ser Val Ser Val Ala Pro Gly Gln Thr Ala Arg Ile Thr Cys Gly
            180                 185                 190

Gly Asn Asn Ile Gly Ser Lys Ser Val His Trp Tyr Gln Gln Lys Pro
        195                 200                 205

Gly Gln Ala Pro Val Leu Val Val Tyr Asp Asp Ser Asp Arg Pro Ser
    210                 215                 220

Gly Ile Pro Glu Arg Phe Ser Gly Ser Asn Ser Gly Asn Thr Ala Thr
225                 230                 235                 240

Leu Thr Ile Ser Arg Val Glu Ala Gly Asp Glu Ala Asp Tyr Tyr Cys
                245                 250                 255

Gln Val Trp Asp Ser Ser Ser Asp Leu Val Val Phe Gly Gly Gly Thr
                260                 265                 270

Lys Leu Thr Val Leu Gly Asn Ser Gly Gly Gly Ser Gly Gly Gly
                275                 280                 285

Gly Ser Gly Gly Gly Ser Ala Ser Glu Pro Lys Ser Ser Asp Lys
    290                 295                 300

Thr His Thr Cys Pro Pro Cys Pro Ala Pro Glu Phe Glu Gly Ala Pro
305                 310                 315                 320

Ser Val Phe Leu Phe Pro Pro Lys Pro Lys Asp Thr Leu Met Ile Ser
                325                 330                 335

Arg Thr Pro Glu Val Thr Cys Val Val Val Asp Val Ser His Glu Asp
                340                 345                 350

Pro Glu Val Lys Phe Asn Trp Tyr Val Asp Gly Val Glu Val His Asn
                355                 360                 365

Ala Lys Thr Lys Pro Arg Glu Glu Gln Tyr Asn Ser Thr Tyr Arg Val
        370                 375                 380

Val Ser Val Leu Thr Val Leu His Gln Asp Trp Leu Asn Gly Lys Glu
385                 390                 395                 400

Tyr Lys Cys Lys Val Ser Asn Lys Ala Leu Pro Thr Pro Ile Glu Lys
                405                 410                 415

Thr Ile Ser Lys Ala Lys Gly Gln Pro Arg Glu Pro Gln Val Tyr Thr
                420                 425                 430

Leu Pro Pro Ser Arg Asp Glu Leu Thr Lys Asn Gln Val Ser Leu Thr
        435                 440                 445

Cys Leu Val Lys Gly Phe Tyr Pro Ser Asp Ile Ala Val Glu Trp Glu
450                 455                 460

Ser Asn Gly Gln Pro Glu Asn Asn Tyr Lys Thr Thr Pro Pro Val Leu
465                 470                 475                 480

Asp Ser Asp Gly Ser Phe Phe Leu Tyr Ser Lys Leu Thr Val Asp Lys
                485                 490                 495

Ser Arg Trp Gln Gln Gly Asn Val Phe Ser Cys Ser Val Met His Glu
                500                 505                 510

Ala Leu His Asn His Tyr Thr Gln Lys Ser Leu Ser Leu Ser Pro Gly
        515                 520                 525

Lys Asp Pro Gly Trp Ser His Pro Gln Phe Glu Lys Ser Ser Gly Gly
        530                 535                 540

Gly Gly Gln Val Gln Leu Gln Glu Ser Gly Pro Gly Leu Val Thr Pro
545                 550                 555                 560

Ser Gln Ser Leu Ser Ile Thr Cys Thr Val Ser Gly Phe Ser Leu Ser
                565                 570                 575

Asp Tyr Gly Val His Trp Val Arg Gln Ser Pro Gly Gln Gly Leu Glu
                580                 585                 590
```

```
Trp Leu Gly Val Ile Trp Ala Gly Gly Thr Asn Tyr Asn Ser Ala
            595                 600                 605

Leu Met Ser Arg Lys Ser Ile Ser Lys Asp Asn Ser Lys Ser Gln Val
            610                 615                 620

Phe Leu Lys Met Asn Ser Leu Gln Ala Asp Asp Thr Ala Val Tyr Tyr
625                 630                 635                 640

Cys Ala Arg Asp Lys Gly Tyr Ser Tyr Tyr Tyr Ser Met Asp Tyr Trp
                645                 650                 655

Gly Gln Gly Thr Thr Val Thr Val Ser Ser Arg Gly Gly Gly Ser Gly
            660                 665                 670

Gly Gly Gly Ser Gly Gly Gly Ser Asp Ile Glu Leu Thr Gln Ser
            675                 680                 685

Pro Ala Ser Leu Ala Val Ser Leu Gly Gln Arg Ala Thr Ile Ser Cys
            690                 695                 700

Arg Ala Ser Glu Ser Val Glu Tyr Tyr Val Thr Ser Leu Met Gln Trp
705                 710                 715                 720

Tyr Gln Gln Lys Pro Gly Gln Pro Pro Lys Leu Leu Ile Phe Ala Ala
                725                 730                 735

Ser Asn Val Glu Ser Gly Val Pro Ala Arg Phe Ser Gly Ser Gly Ser
            740                 745                 750

Gly Thr Asn Phe Ser Leu Asn Ile His Pro Val Asp Glu Asp Asp Val
            755                 760                 765

Ala Met Tyr Phe Cys Gln Gln Ser Arg Lys Val Pro Tyr Thr Phe Gly
            770                 775                 780

Gly Gly Thr Lys Leu Glu Ile Lys Arg
785                 790

<210> SEQ ID NO 45
<211> LENGTH: 792
<212> TYPE: PRT
<213> ORGANISM: Artificial Sequence
<220> FEATURE:
<223> OTHER INFORMATION: Anti-HBsAg scFv [C8]^Glycin-Serin-Linker^hIgG1-
      Fc[C245S,L259F,L26 0E,G262A,A355T]^StrepTag^Glycin-Linker^
      StrepTag^anti-CD16 scFv [A9]

<400> SEQUENCE: 45

Met Asp Phe Glu Val Gln Ile Phe Ser Phe Leu Leu Ile Ser Ala Ser
1               5                   10                  15

Val Ile Met Ser Arg Met Ala Glu Val Gln Leu Val Glu Ser Gly Gly
                20                  25                  30

Gly Leu Leu Gln Pro Gly Gly Ser Leu Arg Leu Ser Cys Ala Ala Ser
            35                  40                  45

Gly Phe Thr Phe Ser Gly Tyr Ala Met Ser Trp Val Arg Gln Ala Pro
        50                  55                  60

Gly Lys Gly Leu Glu Trp Val Ser Ser Ile Ser Gly Ser Gly Gly Ser
65                  70                  75                  80

Thr Tyr Tyr Ala Asp Ser Val Lys Gly Arg Phe Thr Ile Ser Arg Asp
                85                  90                  95

Asn Ser Lys Asn Thr Leu Tyr Leu Gln Met Asn Ser Leu Arg Ala Glu
            100                 105                 110

Asp Thr Ala Leu Tyr Tyr Cys Ala Lys Pro Pro Gly Arg Gln Glu Tyr
        115                 120                 125

Tyr Gly Ser Ser Ile Tyr Tyr Phe Pro Leu Gly Asn Trp Gly Gln Gly
    130                 135                 140

Thr Leu Val Thr Val Ser Ser Ala Ser Thr Lys Gly Pro Lys Leu Glu
```

```
            145                 150                 155                 160
Glu Gly Glu Phe Ser Glu Ala Arg Val Gln Ser Ala Leu Thr Gln Pro
                165                 170                 175
Ala Ser Val Ser Val Ala Pro Gly Gln Thr Ala Arg Ile Thr Cys Gly
            180                 185                 190
Gly Asn Asn Ile Gly Ser Lys Ser Val His Trp Tyr Gln Gln Lys Pro
            195                 200                 205
Gly Gln Ala Pro Val Leu Val Val Tyr Asp Asp Ser Asp Arg Pro Ser
    210                 215                 220
Gly Ile Pro Glu Arg Phe Ser Gly Ser Asn Ser Gly Asn Thr Ala Thr
225                 230                 235                 240
Leu Thr Ile Ser Arg Val Glu Ala Gly Asp Glu Ala Asp Tyr Tyr Cys
                245                 250                 255
Gln Val Trp Asp Ser Ser Ser Asp Leu Val Val Phe Gly Gly Gly Thr
                260                 265                 270
Lys Leu Thr Val Leu Gly Asn Ser Gly Gly Gly Ser Gly Gly Gly
                275                 280                 285
Gly Ser Gly Gly Gly Ser Ala Ser Glu Pro Lys Ser Ser Asp Lys
    290                 295                 300
Thr His Thr Cys Pro Pro Cys Pro Ala Pro Glu Phe Glu Gly Ala Pro
305                 310                 315                 320
Ser Val Phe Leu Phe Pro Pro Lys Pro Lys Asp Thr Leu Met Ile Ser
                325                 330                 335
Arg Thr Pro Glu Val Thr Cys Val Val Val Asp Val Ser His Glu Asp
                340                 345                 350
Pro Glu Val Lys Phe Asn Trp Tyr Val Asp Gly Val Glu Val His Asn
                355                 360                 365
Ala Lys Thr Lys Pro Arg Glu Glu Gln Tyr Asn Ser Thr Tyr Arg Val
    370                 375                 380
Val Ser Val Leu Thr Val Leu His Gln Asp Trp Leu Asn Gly Lys Glu
385                 390                 395                 400
Tyr Lys Cys Lys Val Ser Asn Lys Ala Leu Pro Thr Pro Ile Glu Lys
                405                 410                 415
Thr Ile Ser Lys Ala Lys Gly Gln Pro Arg Glu Pro Gln Val Tyr Thr
                420                 425                 430
Leu Pro Pro Ser Arg Asp Glu Leu Thr Lys Asn Gln Val Ser Leu Thr
                435                 440                 445
Cys Leu Val Lys Gly Phe Tyr Pro Ser Asp Ile Ala Val Glu Trp Glu
    450                 455                 460
Ser Asn Gly Gln Pro Glu Asn Asn Tyr Lys Thr Thr Pro Pro Val Leu
465                 470                 475                 480
Asp Ser Asp Gly Ser Phe Phe Leu Tyr Ser Lys Leu Thr Val Asp Lys
                485                 490                 495
Ser Arg Trp Gln Gln Gly Asn Val Phe Ser Cys Ser Val Met His Glu
                500                 505                 510
Ala Leu His Asn His Tyr Thr Gln Lys Ser Leu Ser Leu Ser Pro Gly
                515                 520                 525
Lys Asp Pro Gly Trp Ser His Pro Gln Phe Glu Lys Ser Arg Gly Gly
                530                 535                 540
Gly Gly Gln Val Gln Leu Gln Gln Ser Gly Ala Glu Leu Val Arg Pro
545                 550                 555                 560
Gly Thr Ser Val Lys Ile Ser Cys Lys Ala Ser Gly Tyr Thr Phe Thr
                565                 570                 575
```

-continued

```
Asn Tyr Trp Leu Gly Trp Val Lys Gln Arg Pro Gly His Gly Leu Glu
                580                 585                 590
Trp Ile Gly Asp Ile Tyr Pro Gly Gly Tyr Thr Asn Tyr Asn Glu
            595                 600                 605
Lys Phe Lys Gly Lys Ala Thr Val Thr Ala Asp Thr Ser Ser Arg Thr
610                 615                 620
Ala Tyr Val Gln Val Arg Ser Leu Thr Ser Glu Asp Ser Ala Val Tyr
625                 630                 635                 640
Phe Cys Ala Arg Ser Ala Ser Trp Tyr Phe Asp Val Trp Gly Ala Gly
                645                 650                 655
Thr Thr Val Thr Val Ser Ser Gly Asn Ser Gly Gly Gly Gly Ser Gly
                660                 665                 670
Gly Gly Ser Gly Gly Gly Ser Ala Ser Gln Ala Val Val Thr
            675                 680                 685
Gln Glu Ser Ala Leu Thr Thr Ser Pro Gly Glu Thr Val Thr Leu Thr
690                 695                 700
Cys Arg Ser Asn Thr Gly Thr Val Thr Thr Ser Asn Tyr Ala Asn Trp
705                 710                 715                 720
Val Gln Glu Lys Pro Asp His Leu Phe Thr Gly Leu Ile Gly His Thr
                725                 730                 735
Asn Asn Arg Ala Pro Gly Val Pro Ala Arg Phe Ser Gly Ser Leu Ile
                740                 745                 750
Gly Asp Lys Ala Ala Leu Thr Ile Thr Gly Ala Gln Thr Glu Asp Glu
            755                 760                 765
Ala Ile Tyr Phe Cys Ala Leu Trp Tyr Asn Asn His Trp Val Phe Gly
770                 775                 780
Gly Gly Thr Lys Leu Thr Val Leu
785                 790

<210> SEQ ID NO 46
<211> LENGTH: 799
<212> TYPE: PRT
<213> ORGANISM: Artificial Sequence
<220> FEATURE:
<223> OTHER INFORMATION: Anti-HBsAg scFv [C8]^Glycin-Serin-Linker^hIgG1-
    Fc[C245S,L259F,L26 0E,G262A,A355T]^StrepTag^Glycin-Linker^
    StrepTag^anti-CD56 scFv [NCAM29.2]

<400> SEQUENCE: 46

Met Asp Phe Glu Val Gln Ile Phe Ser Phe Leu Leu Ile Ser Ala Ser
1               5                   10                  15
Val Ile Met Ser Arg Met Ala Glu Val Gln Leu Val Glu Ser Gly Gly
                20                  25                  30
Gly Leu Leu Gln Pro Gly Gly Ser Leu Arg Leu Ser Cys Ala Ala Ser
            35                  40                  45
Gly Phe Thr Phe Ser Gly Tyr Ala Met Ser Trp Val Arg Gln Ala Pro
        50                  55                  60
Gly Lys Gly Leu Glu Trp Val Ser Ser Ile Ser Gly Ser Gly Gly Ser
65                  70                  75                  80
Thr Tyr Tyr Ala Asp Ser Val Lys Gly Arg Phe Thr Ile Ser Arg Asp
                85                  90                  95
Asn Ser Lys Asn Thr Leu Tyr Leu Gln Met Asn Ser Leu Arg Ala Glu
                100                 105                 110
Asp Thr Ala Leu Tyr Tyr Cys Ala Lys Pro Pro Gly Arg Gln Glu Tyr
            115                 120                 125
```

-continued

Tyr Gly Ser Ser Ile Tyr Tyr Phe Pro Leu Gly Asn Trp Gly Gln Gly
    130                 135                 140

Thr Leu Val Thr Val Ser Ser Ala Ser Thr Lys Gly Pro Lys Leu Glu
145                 150                 155                 160

Glu Gly Glu Phe Ser Glu Ala Arg Val Gln Ser Ala Leu Thr Gln Pro
            165                 170                 175

Ala Ser Val Ser Val Ala Pro Gly Gln Thr Ala Arg Ile Thr Cys Gly
        180                 185                 190

Gly Asn Asn Ile Gly Ser Lys Ser Val His Trp Tyr Gln Gln Lys Pro
    195                 200                 205

Gly Gln Ala Pro Val Leu Val Val Tyr Asp Asp Ser Asp Arg Pro Ser
210                 215                 220

Gly Ile Pro Glu Arg Phe Ser Gly Ser Asn Ser Gly Asn Thr Ala Thr
225                 230                 235                 240

Leu Thr Ile Ser Arg Val Glu Ala Gly Asp Glu Ala Asp Tyr Tyr Cys
            245                 250                 255

Gln Val Trp Asp Ser Ser Ser Asp Leu Val Val Phe Gly Gly Gly Thr
        260                 265                 270

Lys Leu Thr Val Leu Gly Asn Ser Gly Gly Gly Ser Gly Gly Gly
    275                 280                 285

Gly Ser Gly Gly Gly Ser Ala Ser Glu Pro Lys Ser Ser Asp Lys
290                 295                 300

Thr His Thr Cys Pro Pro Cys Pro Ala Pro Glu Phe Glu Gly Ala Pro
305                 310                 315                 320

Ser Val Phe Leu Phe Pro Pro Lys Pro Lys Asp Thr Leu Met Ile Ser
            325                 330                 335

Arg Thr Pro Glu Val Thr Cys Val Val Val Asp Val Ser His Glu Asp
        340                 345                 350

Pro Glu Val Lys Phe Asn Trp Tyr Val Asp Gly Val Glu Val His Asn
            355                 360                 365

Ala Lys Thr Lys Pro Arg Glu Glu Gln Tyr Asn Ser Thr Tyr Arg Val
    370                 375                 380

Val Ser Val Leu Thr Val Leu His Gln Asp Trp Leu Asn Gly Lys Glu
385                 390                 395                 400

Tyr Lys Cys Lys Val Ser Asn Lys Ala Leu Pro Thr Pro Ile Glu Lys
            405                 410                 415

Thr Ile Ser Lys Ala Lys Gly Gln Pro Arg Glu Pro Gln Val Tyr Thr
        420                 425                 430

Leu Pro Pro Ser Arg Asp Glu Leu Thr Lys Asn Gln Val Ser Leu Thr
    435                 440                 445

Cys Leu Val Lys Gly Phe Tyr Pro Ser Asp Ile Ala Val Glu Trp Glu
450                 455                 460

Ser Asn Gly Gln Pro Glu Asn Asn Tyr Lys Thr Thr Pro Pro Val Leu
465                 470                 475                 480

Asp Ser Asp Gly Ser Phe Phe Leu Tyr Ser Lys Leu Thr Val Asp Lys
            485                 490                 495

Ser Arg Trp Gln Gln Gly Asn Val Phe Ser Cys Ser Val Met His Glu
        500                 505                 510

Ala Leu His Asn His Tyr Thr Gln Lys Ser Leu Ser Leu Ser Pro Gly
    515                 520                 525

Lys Asp Pro Gly Trp Ser His Pro Gln Phe Glu Lys Ser Ser Gly Gly
530                 535                 540

Gly Gly Asp Val Gln Leu Val Glu Ser Gly Gly Gly Leu Val Gln Pro

```
                545                 550                 555                 560
    Gly Gly Ser Arg Lys Leu Ser Cys Ala Ala Ser Gly Phe Thr Phe Ser
                    565                 570                 575

Ser Phe Gly Met His Trp Val Arg Gln Ala Pro Glu Lys Gly Leu Glu
                    580                 585                 590

Trp Val Ala Tyr Ile Ser Ser Gly Ser Tyr Ala Ile Tyr Tyr Ala Asp
                    595                 600                 605

Thr Val Lys Gly Arg Phe Thr Ile Ser Arg Asp Asn Pro Glu Asn Thr
                    610                 615                 620

Leu Phe Leu Gln Met Thr Ser Leu Arg Ser Glu Asp Ser Ala Met Tyr
    625                 630                 635                 640

Tyr Cys Val Arg Gly Arg Arg Leu Gly Glu Gly Tyr Ala Met Asp Tyr
                    645                 650                 655

Trp Gly Gln Gly Thr Ser Val Thr Val Ser Ser Gly Asn Ser Gly Gly
                    660                 665                 670

Gly Gly Ser Gly Gly Gly Gly Ser Gly Gly Gly Gly Ser Ala Ser Asp
                    675                 680                 685

Ile Val Met Ser Gln Ser Pro Ser Ser Leu Ala Val Ser Val Gly Glu
                    690                 695                 700

Lys Val Thr Met Ser Cys Lys Ser Ser Gln Ser Leu Leu Tyr Ser Ser
    705                 710                 715                 720

Asn Gln Lys Asn Tyr Leu Ala Trp Tyr Gln Gln Lys Pro Gly Gln Ser
                    725                 730                 735

Pro Lys Leu Leu Ile Tyr Trp Ala Ser Thr Arg Lys Ser Gly Val Pro
                    740                 745                 750

Asp Arg Phe Thr Gly Ser Gly Ser Gly Thr Asp Phe Thr Leu Thr Ile
                    755                 760                 765

Ser Ser Val Lys Ala Glu Asp Leu Ala Val Tyr Tyr Cys Gln Gln Tyr
                    770                 775                 780

Ser Ser Trp Thr Phe Gly Gly Gly Thr Lys Leu Glu Ile Lys Arg
    785                 790                 795

<210> SEQ ID NO 47
<211> LENGTH: 15
<212> TYPE: PRT
<213> ORGANISM: Artificial Sequence
<220> FEATURE:
<223> OTHER INFORMATION: Linker

<400> SEQUENCE: 47

Gly Gly Gly Gly Ser Gly Gly Gly Gly Ser Gly Gly Gly Gly Ser
1               5                   10                  15

<210> SEQ ID NO 48
<211> LENGTH: 17
<212> TYPE: PRT
<213> ORGANISM: Artificial Sequence
<220> FEATURE:
<223> OTHER INFORMATION: Linker

<400> SEQUENCE: 48

Ala Lys Thr Thr Pro Lys Leu Glu Glu Gly Glu Phe Ser Glu Ala Arg
1               5                   10                  15
Val

<210> SEQ ID NO 49
<211> LENGTH: 20
<212> TYPE: PRT
```

```
<213> ORGANISM: Artificial Sequence
<220> FEATURE:
<223> OTHER INFORMATION: Linker

<400> SEQUENCE: 49

Gly Gly Gly Gly Ser Gly Gly Gly Gly Ser Gly Gly Gly Gly Ser Gly
1               5                   10                  15

Gly Gly Gly Ser
            20
```